USOO5747503A

United States Patent [19]
Rothman et al.

[11] Patent Number: 5,747,503
[45] Date of Patent: May 5, 1998

[54] SELECTIVE INHIBITORS OF BIOGENIC AMINE TRANSPORTERS

[75] Inventors: Richard Rothman, Silver Spring, Md.; Frank I. Carroll, Durham, N.C.; Bruce Blough, Raleigh, N.C.; Samuel W. Mascarella, Hillsborough, N.C.

[73] Assignees: The United States of America as represented by the Department of Health and Human Services, Washington, D.C.; Research Triangle Institute, Research Triangle Park, N.C.

[21] Appl. No.: 746,517

[22] Filed: Nov. 12, 1996

Related U.S. Application Data

[60] Division of Ser. No. 203,222, Feb. 28, 1994, Pat. No. 5,574,060, which is a continuation-in-part of Ser. No. 105,747, Aug. 12, 1993, abandoned.

[51] Int. Cl.⁶ .................... C07D 221/22; A61K 31/46
[52] U.S. Cl. .................... 514/294; 514/299; 546/94; 546/95; 546/112; 546/183
[58] Field of Search ....................... 546/112, 183, 546/94, 95; 514/294, 299

[56] References Cited

PUBLICATIONS

Kametani et. al., "Studies on . . . Benzazocine", Journal of Heterocyclic Chemistry, vol. 10 (1973), pp. 291–295.
Blough et. al., "Synthesis of . . . Benzazocine", Journal of Chem. Soc., Chem. Comm., No. 9 (1993), pp. 758–760.

*Primary Examiner*—Matthew V. Grumbling
*Assistant Examiner*—Tamthom T. Ngo

*Attorney, Agent, or Firm*—Morgan & Finnegan, L.L.P.

[57] ABSTRACT

The present invention provides a compound having the structure:

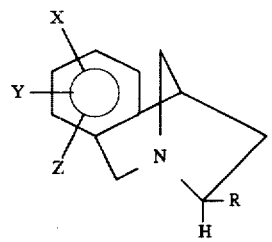

wherein X, Y, and Z are independently H, Cl, Br, F, OCH₃, I, or an alkyl group having 1 to 6 carbon atoms; and R is

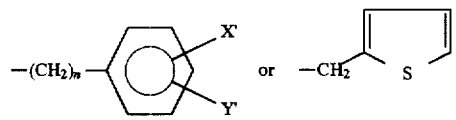

wherein n is 0 to 6, X' and Y' are independently H, Cl, F, CH₃, C₂H₅, C₃H₇, C₄H₉, OCH₃, OH, CF₃, OCF₃, NO₂, NH₂, N(CH₃)₂, NHCOCH₃, NCS, NHCOCH₂Br, or N₃, and (CH₂)ₙ, if present, may be substituted with OH, OCH₃, or an alkyl or alkenyl group having 1 to 3 carbon atoms. The present invention also provides a pharmaceutical composition comprising the compound above and a pharmaceutically acceptable carrier. The present invention further provides a method for treating a disease characterized by a dopamine deficiency which comprises administering to a subject in need of such treatment an amount of the pharmaceutical composition above effective to treat the disease.

70 Claims, 5 Drawing Sheets

SELECTIVE INHIBITORS OF BIOGENIC AMINE TRANSPORTERS

This is a divisional of application Ser. No. 08/203,222 filed Feb. 28, 1994, U.S. Pat. No. 5,574,060 which is a continuation-in-part of Ser. No. 08/105,747, filed Aug. 12, 1993, now abandoned.

BACKGROUND OF THE INVENTION

[$^3$H]1-[1-(2-thienyl)cyclohexyl]cyclohexyl]-piperidine (TCP), an analog of the dissociative anesthetic phencyclidine (PCP), binds with high affinity to two sites in guinea pig brain membranes, one of which is MK-801 sensitive and one of which is not. The MK-801-sensitive site (PCP site 1) is associated with NMDA receptors. The MK-801-insensitive site (PCP site 2) is thought to be associated with biogenic amine transporters (BAT) (Rothman, R. B., et al. *Mol. Pharmacol.* 36: 887–896 (1989); Akunne, H. C., et al. *Synapse* 8: 289–300 (1991); Rothman, R. B., et al., In: *Multiple Sigma and PCP Receptor Ligands: Mechanisms for Neuromodulation and Protection*, pp. 137–146 (Domino, E. F. and Kamenka, J. M., eds., 1992); Akunne, H. C., et al. *Neurochem. Res.* 17: 261–264 (1992)).

Based upon the association of PCP site 2 with BATs, drugs with high affinity for PCP site 2 would be expected to inhibit the reuptake of biogenic amines.

The present invention is directed to classes of compounds which bind selectively and potently to PCP site 2 and also have activity as biogenic amine transport blockers. (2RS, 3aSR, 8aRS)-1,2,3a,8,8a-Hexahydro-2-benzyl-1-methyl-indeno[1,2-b]pyrrole (RTI-4793–14) represents the first of these compounds which bind with high affinity to biogenic amine transporters but are relatively less potent amine reuptake blockers than classical BAT ligands. This compound has been shown to increase the levels of dopamine in the brain and thus would be useful for treating diseases or disorders characterized by dopamine deficiency such as Parkinson's Disease and depression. The compound also would be useful in radioligand binding studies to label the PCP site 2 because of its high affinity and selectively for PCP site 2.

Hungarian Patent No. 151,567 disclosed ideno [1,2-b] pyrroles having the structure below wherein R1 is hydrogen, aryl, or a heteroaryl group and R2 is a H or an alkyl group (see also Chemical Abstracts, vol. 62, No. 528(g) (1965)). Some of these compounds have antispasmatic or tranquilizing properties.

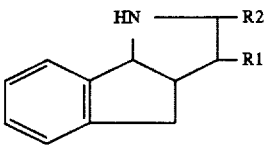

De and Saha disclosed ideno [1,2-b]pyrroles having the structure below wherein R is an alkyl group such as methyl, ethyl, propyl, butyl, or pentyl (De, A. U. and Saha, B. P., *J. Pharm. Sci.* 62(8): 1363–1364 (1973);

De, A. U. and Saha, B. P., *J. Pharm. Sci.* 64(2): 249–252 (1975)). These compounds were screened as possible oral hypoglycemic agents.

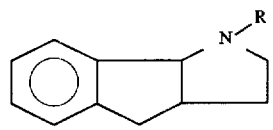

SUMMARY OF THE INVENTION

The present invention provides a compound having the structure:

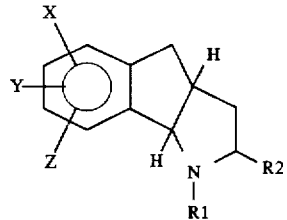

wherein X, Y, and Z are independently H, Cl, Br, F, OCH$_3$, I, or an alkyl group having 1 to 6 carbon atoms; R1 is H, an alkyl or alkenyl group having 1 to 6 carbon atoms, or

and R2 is

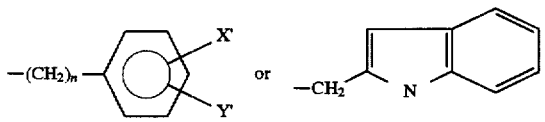

wherein n is 0 to 6, X' and Y' are independently H, Cl, F, CH$_3$, C$_2$H$_5$, C$_3$H$_7$, C$_4$H$_9$, OCH$_3$, OH, CF$_3$, OCF$_3$, NO$_2$, NH$_2$N(CH$_3$)$_2$, NHCOCH$_3$, NCS, NHCOCH$_2$Br, or N$_3$, and (CH$_2$)$_n$ if present, may be substituted with OH, OCH$_3$, or an alkyl or alkenyl group having 1 to 3 carbon atoms.

The present invention also provides a compound having the structure:

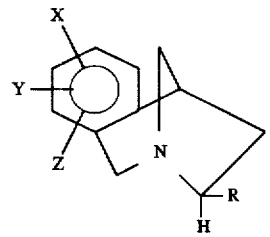

wherein X, Y, and Z are independently H, Cl, Br, F, OCH$_3$, I, or an alkyl group having 1 to 6 carbon atoms; and R is

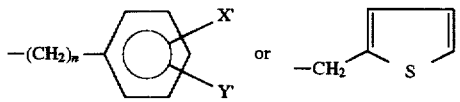

wherein n is 0 to 6, X' and Y' are independently H, Cl, F, CH$_3$, C$_2$H$_5$, C$_3$H$_7$, C$_4$H$_9$, OCH$_3$, OH, CF$_3$, OCF$_3$, NO$_2$, NH$_2$N(CH$_3$)$_2$, NHCOCH$_3$, NCS, NHCOCH$_2$Br, or N$_3$, and (CH$_2$)$_n$, if present, may be substituted with OH, OCH$_3$, or an alkyl or alkenyl group having 1 to 3 carbon atoms.

The present invention further provides a compound having the structure:

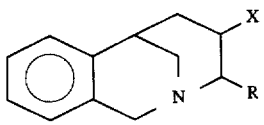

wherein X is H, Cl, Br, F, OCH$_3$, I, or an alkyl group having 1 to 6 carbon atoms; and R is

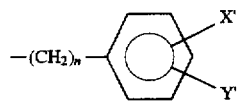

wherein n is 0 to 6, X' and Y' are independently H, Cl, F, CH$_3$, C$_2$H$_5$, C$_3$H$_7$, C$_4$H$_9$, OCH$_3$, OH, CF$_3$, OCF$_3$, NO$_2$, NH$_2$, N(CH$_3$)$_2$, NHCOCH$_3$, NCS, NHCOCH$_2$Br, or N$_3$, and (CH$_2$)$_n$, if present, may be substituted with OH, OCH$_3$, or an alkyl or alkenyl group having 1 to 3 carbon atoms.

The present invention also provides a pharmaceutical composition comprising one of the compounds above and a pharmaceutically acceptable carrier.

Lastly, the present invention provides a method for treating a disease characterized by a dopamine deficiency which comprises administering to a subject in need of such treatment an amount of the pharmaceutical composition above effective to treat the disease.

DETAILED DESCRIPTION OF THE INVENTION

Figure 1:
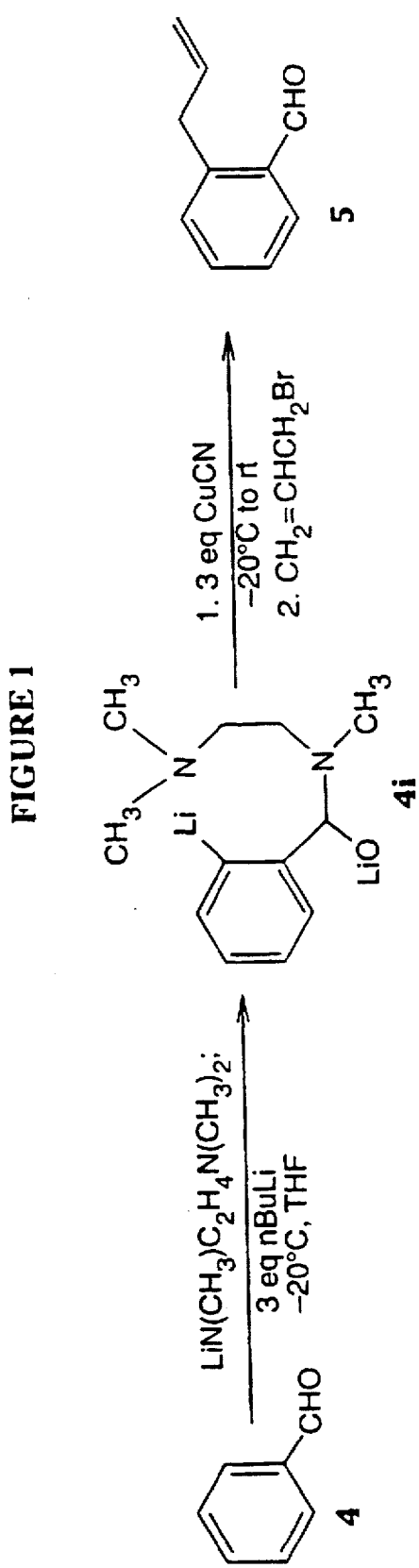
FIG. 1. Schematic diagram for the synthesis of o-allylbenzaldehyde.

The present invention provides a compound having the structure:

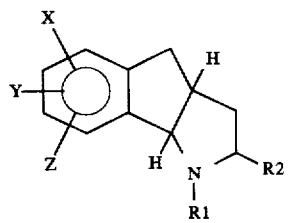

wherein X, Y, and Z are independently H, Cl, Br, F, OCH$_3$, I, or an alkyl group having 1 to 6 carbon atoms; R1 is H, an alkyl or alkenyl group having 1 to 6 carbon atoms, or

and R2 is

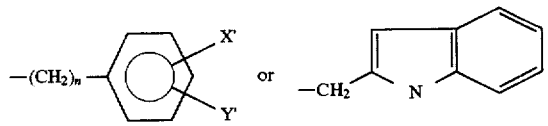

wherein n is 0 to 6, X' and Y' are independently H, Cl, F, CH$_3$, C$_2$H$_5$, C$_3$H$_7$, C$_4$H$_9$, OCH$_3$, OH, CF$_3$, OCF$_3$, NO$_2$, NH$_2$N(CH$_3$)$_2$, NHCOCH$_3$, NCS, NHCOCH$_2$Br, or N$_3$, and (CH$_2$)$_n$, if present, may be substituted with OH, OCH$_3$, or an alkyl or alkenyl group having 1 to 3 carbon atoms. The compounds of the present invention may exist in (2R, 3aS, 8aR)-, (2S, 3aS, 8aR)-, (2R, 3aR, 8aS)-, or (2S, 3aR, 8aS)-isomers, or mixtures thereof.

In the preferred embodiment, R2 is a substituted or unsubstituted benzyl group. The benzyl group may be substituted with one or more of the following: H, Cl, F, CH$_3$, C$_2$H$_5$, C$_3$H$_7$, C$_4$H$_9$, OCH$_3$, OH, CF$_3$, OCF$_3$, NO$_2$, NH$_2$, N(CH$_3$)$_2$, NHCOCH$_3$, NCS, NHCOCH$_2$Br, or N$_3$. In the more preferred embodiment, R1 is methyl and R2 is benzyl. Most preferably, R1 is methyl, R2 is benzyl, and X, Y, and Z are hydrogen.

The present invention also provides a compound having the structure:

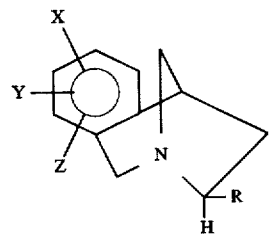

wherein X, Y, and Z are independently H, Cl, Br, F, OCH$_3$, I, or an alkyl group having 1 to 6 carbon atoms; and R is

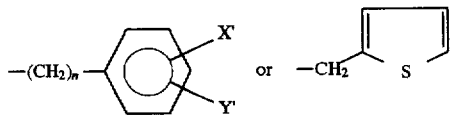

wherein n is 0 to 6, X' and Y' are independently H, Cl, F, CH$_3$, C$_2$H$_5$, C$_3$H$_7$, C$_4$H$_9$, OCH$_3$, OH, CF$_3$, OCF$_3$, NO$_2$, NH$_2$, N(CH$_3$)$_2$, NHCOCH$_3$, NCS, NHCOCH$_2$Br, or N$_3$, and (CH$_2$)$_n$, if present, may be substituted with OH, OCH$_3$, or an alkyl or alkenyl group having 1 to 3 carbon atoms. The compounds of the present invention may exist as isomers, or mixtures thereof.

In the preferred embodiment, R is a substituted or unsubstituted benzyl group. The benzyl group may be substituted with one or more of the following: H, Cl, F, CH$_3$, C$_2$H$_5$, C$_3$H$_7$, C$_4$H$_9$, OCH$_3$, OH, CF$_3$, OCF$_3$, NO$_2$, NH$_2$, N(CH$_3$)$_2$, NHCOCH$_3$, NCS, NHCOCH$_2$Br, or N$_3$. In the more preferred embodiment, R is benzyl and X, Y, and Z are hydrogen, and most preferably, the compound is the (+) optical isomer.

The present invention further provides a compound having the structure:

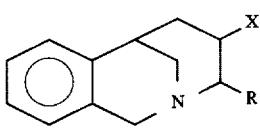

wherein X is H, Cl, Br, F, OCH₃, I, or an alkyl group having 1 to 6 carbon atoms; and R is

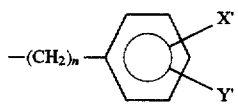

wherein n is 0 to 6, X' and Y' are independently H, Cl, F, CH₃, C₂H₅, C₃H₇, C₄H₉, OCH₃, OH, CF₃, OCF₃, NO₂, NH₂N(CH₃)₂, NHCOCH₃, NCS, NHCOCH₂Br, or N₃, and (CH₂)ₙ, if present, may be substituted with OH, OCH₃, or an alkyl or alkenyl group having 1 to 3 carbon atoms. The compounds of the present invention may exist as isomers, or mixtures thereof.

In the preferred embodiment, R is phenyl. In the more preferred embodiment, X is bromo or hydrogen, and most preferably, X is hydrogen.

The present invention also provides a pharmaceutical composition comprising one of the compound above, or a mixture of the compounds and a pharmaceutically acceptable carrier. The carrier must be "acceptable" in the sense of being compatible with the other ingredients of the formulation and not deleterious to the recipient thereof. The concentration of the compound present in the formulation will depend upon the choice of carrier as well as the results desired.

Examples of suitable pharmaceutical carriers include lactose, sucrose, starch, talc magnesium stearate, crystalline cellulose, methyl cellulose, carboxymethyl cellulose, glycerin, sodium alginate, gum arabic, powders, saline, water, among others. The choice of carrier will depend upon the route of administration. The formulations may conveniently be presented in unit dosage and may be prepared by methods well-known in the pharmaceutical art.

For intravenous intramuscular, subcutaneous, or intraperitoneal administration, the compound is combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For oral administration, the compound is combined with various powders and formulated into tablets or capsules by methods known in the art.

The present invention also provides a method for treating a disease characterized by a dopamine deficiency which comprises administering to a subject in need of such treatment an amount of the pharmaceutical composition above effective to treat the disease.

Preferably, the disease is Parkinson's disease or depression. However, the method may be employed to treat any disease characterized by a dopamine deficiency.

The administration may be affected by means known to those skilled in the art such as oral, intravenous, subcutaneous, intramuscular, or intraperitoneal routes of administration.

The effective amount is preferably between about 1 μg/kg and about 10 mg/kg. The actual dose will depend upon the route of administration, the pharmacokinetic properties of the individual treated, as well as the results desired.

The present invention is described in the following Experimental Details section, which sets forth specific examples to aid in an understanding of the invention, and should not be construed to limit in any way the invention as defined in the claims which follow thereafter.

Experimental Details Section

Chemicals

All chemicals used in chemical synthesis may be obtained from Aldrich Chemical Company (Milwaukee, Wis.). [³H] TCP (40.8 Ci/mmol), [³H]DA (47 Ci/mmol), [³H]5-HT (28.2 Ci/mmol), [³H](+)-MK801 (30 Ci/mmol), and [³H]-CFT (80.1 Ci/mmol) were purchased from New England Nuclear (Boston, Mass.). [³H]Nisoxetine (SA=82 Ci/mmol) was purchased from American Radiochemicals. (+)-MK801 and indatraline were purchased from Research Biochemicals Inc. (Natick, Mass.). PCP was obtained from the NIDA Addiction Research Center pharmacy. Frozen guinea pig brains were purchased from Pel-Freeze Laboratories, (Rogers, Ark.). The sources of equipment and reagents required for the in vivo microdialysis studies are as published (Rothman, R. H., et al. *Pharmacol. Biochem. Behav.* 40: 387–397 (1991)).

Chemical Synthesis of RTI-4793-14 and Analogs Thereof

A modified Comins procedure (Comins, D. L., et al. *Tetrahedron Lett.* 3979–3982 (1982)) for functionalizing benzaldehydes at the ortho position was followed (see FIG. 1). Benzaldehyde (4) was first treated with three equivalents of butyllithium at −20° C. in tetrahydrofuran (THF) in the presence of lithium trimethylethylenediamine which serves to protect the aldehyde and to direct the lithiation to the orthoposition, presumably via an intermediate like 4i. Direct allylation of 4i was not successful. However, when 4i were converted to the cyanocuprate prior to treatment with allyl bromide, an 85% yield of 5 was obtained.

Figure 2:
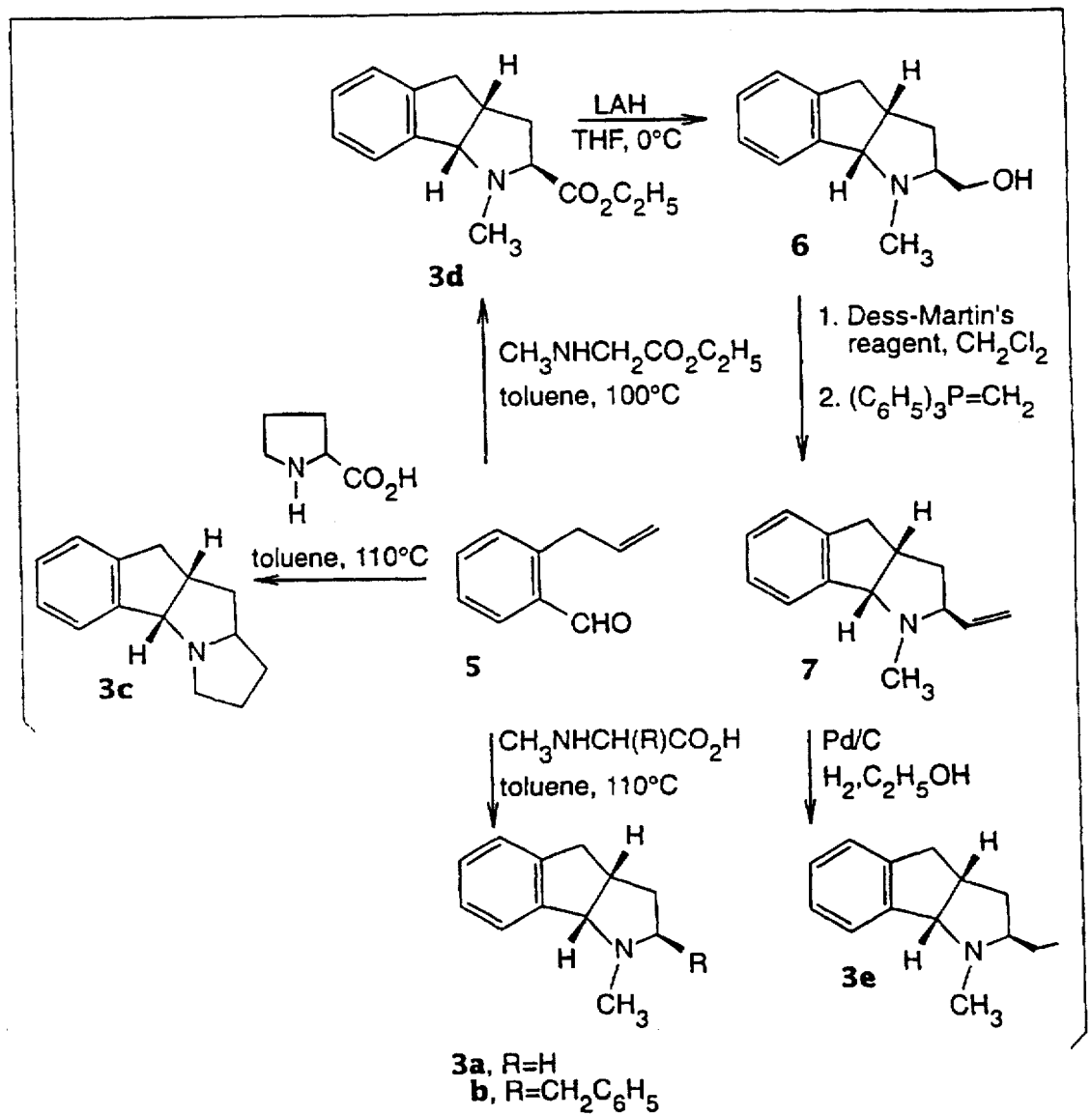
FIG. 2. Schematic diagram for the synthesis of hexahydro-1-methylindeno[1,2-b]pyrroles.

FIG. 2 outlines the reactions used to prepare 3a–e. Subjection of 5 to a [3+2] cycloaddition reaction using ethyl N-methylglycinate in toluene gave an 87% yield of 3d. When N-methylglycine, N-methyl-phenylalanine, or proline were used in the cycloaddition, decarboxylation occurred before cycloaddition to give the desired analogues, 3a–c, respectively. Lithium aluminum hydride reduction of 3d afforded the alcohol 6. Oxidation of 6 using Dess-Martin's reagent afforded an unstable aldehyde which was condensed with methylenetriphenylphosphorane to give the olefin 7 which was catalytically reduced to the desired 3e. The relative stereochemistry of the substituent and the ring junction for 3a–e was shown to be cis by NOE studies. This stereochemistry of the C-2 substituent was expected since ylides normally react thermally in a cisoid conformation. The molecular formulas and melting points (°C.) for compounds 3a–e are as follows: 3a (RTI-4793-12): C₁₉H₂₁NO₄, 88°–91° C.; 3b (RTI-4793-14): C₂₆H₂₇NO₄, 121°–123° C.; 3c (RTI-4793-13): C₂₁H₂₃NO₄, 100° C. (dec); 3d (RTI-4793-7): C₂₂H₂₅NO6, 78°–82° C.; 3e (RTI-4793-9): C₂₁H₂₅NO₄, 110–115° C. All compounds are resorcylate salts. The compounds were analyzed for C, H, and N. The results agreed to within ±0.4% of the theoretical values.

RTI-4793-14 also has been resolved into its two optical isomers, (+)- and (−)-RTI-4793-14, using D- and L-di-p-toluoyltartaric acid.

A detailed discussion of the synthesis of the o-allylbenzaldehyde (4), (3aRS, 8aSR)-1,2,3a,8,8a-Hexahydro-2-benzyl-1-methylindeno[1,2-b]pyrrole (RTI-4793-14) (3b), and its two optical isomers is presented below.

o-Allylbenzaldehyde (4)

To a stirred solution of 20.2 g (198.0 mmol) of lithium trimethylethylenediamine in 500 ml of dry tetrahydrofuran (THF) under nitrogen at −30° C. was added 79 ml (198.0 mmol) of 2.5M butyllithium (nBuLi) in hexanes dropwise over 15 minutes. The solution became pale yellow and was stirred at −30° C. for 30 minutes. To this solution was added 20.0 g (188.5 mmol) of benzaldehyde dropwise over 30 minutes. The solution became cloudy as the complex was formed and was stirred 1 hour. To this slurry was added 113 ml (283 mmol) of 2.5M nBuLi hexanes dropwise over 1 hour. This slurry was stirred for 24 hours and gradually cleared. The solution was then transferred via cannula into a slurry of 50.6 g (565 mmol) of copper cyanide in 500 ml of dry tetrahydrofuran under nitrogen at −78° C. The mixture was allowed to warm to −30° C. and stirred for 30 minutes. To this slurry was added 49 ml (565 mmol) of allyl bromide. The mixture instantly darkened upon addition. The reaction was quenched after 30 minutes with 3% aqueous ammonium hydroxide and saturated ammonium chloride. This biphasic solution was stirred overnight to ensure complete copper removal. The aqueous layer was extracted repetitively with ether to remove all product. The combined organic layers were dried over sodium sulfate and concentrated under reduced pressure. The yellow oil was purified by distillation at 62° C. at 0.03 torr affording 15.32 g (56%) of o-allylbenzaldehyde. $^1$H NMR: δ3.82 (d; 2H, J=6.17 Hz, $CH_2CH=CH_2$), 4.99 (d; 1H, J=17.1 Hz, one of $CH=CH_2$), 5.09 (d; 1H, J=10.2 Hz, one of $CH=CH_2$), 6.04 (m, 1H $CH=CH_2$), 7.3 (d; 1H, J=7.8 Hz, aryl H), 7.40 (dd; 1H, J=7.6 Hz, aryl H), 7.54 (dd; 1H, J=7.4 Hz, 7.8 Hz, aryl H), 7.86 (d; 1H, J=7.6 Hz, aryl H), 10.26 (s; 1H aldehyde H).

(2RS, 3aSR, 8aRS)-1,2,3a,8,8a-Hexahydro-2-benzyl-1-methylindeno[1,2-b]pyrrole (RTI-4793-14) (3b)

A slurry of 0.846 g (3.68 mmol) of N-methylphenylalanine hydrochloride and 0.414 g (2.83 mmol) of o-allylbenzaldehyde was heated to reflux overnight in a mixture of 7 ml of toluene and 7 ml of TMEDA. The apparatus was fitted with Dean-Stark trap to ensure the removal of water. The solution became clearer. The mixture was concentrated under reduced pressure and then diluted with diethyl ether. The amine was extracted out of the organic layer with 1N HCL. The combined aqueous layers were then raised to pH 10 with 1N NaOH and the free base extracted out with methylene chloride. The combined organic layers were dried over sodium sulfate and concentrated under reduced pressure. The crude oil was purified by column chromatography on silica gel. Elution with ether afforded 0.335 g (45%) of RTI-4793-14. $^1$H NMR: δ1.49 (m; 1H, one of $CHCH_2CH$), 1.90 (dt; 1H, J=12.3 Hz, 8.47 Hz, one of $CHCH_2CH$), 2.37 (dd, 1H, J=9.5 Hz, 12.7 Hz, $CH_2CHCH_2$), 2.63 (s; 3H, $CH_3N$), 2.63 (m; 1H, benzyl H), 2.75 (m; 1H, benzyl H and $CH_2CHN$), 4.68 (d; 1H, J=7.1 Hz, $C_6H_4CHN$), 7.12–7.37 (m; 9H, phenyl H).

Isomers of RTI-4793-14

To a solution of 1.545 g (5.87 mmol) of racemic RTI-4793-14 and 2.37 g (5.87 mmol) of di-p-toluoyl-D-tartaric acid monohydrate in a minimal amount of ethyl acetate was added diethyl ether until cloudy. Crystals formed in 4 days and were removed by filtration. The mother liquor was set aside. The crystals were recrystallized 4×from a methanol-ether solution to provide optically pure (+)-RTI-4793-14. The optical purity was found to be >99% ee by HPLC analysis of the free base on a Sumichiral OA-4900 chiral column. $[\alpha]_D$ +88.4° (c 0.83, $CHCl_3$).

Anal. Calcd. for $C_{39}H_{39}NO_8 \cdot 0.25\ H_2O$: C, 71.60; H, 6.09; N, 2.14. Found: C, 71.55; H, 6.03; N, 2.08.

The mother liquor was basified with 1M NaOH.

The aqueous layer was extracted with methylene chloride to provide 0.85 g (3.23 mmol) of enriched (−)-RTI-4793-14 which was dissolved with 1.25 g (3.23 mmol) of di-p-toluoyl-L-tartaric acid in ethyl acetate. Ether was added until cloudy. Crystals formed overnight and were removed by filtration. The crystals were recrystallized 4×from a methanol-ether solution to provide optically pure (−)-RTI-4793-14. The optical purity was found to be >99% ee by HPLC analysis of the free base on a Sumichiral OA-4900 chiral column. $[\alpha]_D$ −88.40 (c 0.505, $CHCl_3$).

Anal. Calcd. for $C_{39}H_{39}NO_8 \cdot 0.25\ H_2O$: C, 71.60; H, 6.09; N, 2.14. Found: C, 71.49; H, 6.00; N, 2.12.

(2RS,3aSR,8bRS)-1,2,3,3a,4,8b-Hexahydro-2-(4-chlorobenzyl)-1-methylindeno-[1,2-b]pyrrole Hydrochloride (RTI-4793-45)

o-Allylbenzaldehyde (0.584 g) was suspended in a solution of 10 ml each of toluene and TMEDA in a round-bottom flask fitted with a Dean-Stark trap. N-Methyl-p-chlorophenylalanine hydrochloride (1.00 g) was added, and the solution was heated to reflux for 16 hours. After removal of the solvents, 1N HCl was added to the residue, and the pH of the solution was adjusted to 2. Ether was added, and the organic layer was extracted with $H_2O$ (3×50 ml). The combined aqueous layers were basified with ammonium hydroxide and extracted with methylene chloride (3×100 ml). The combined organic layers were dried ($Na_2SO_4$), filtered, and concentrated in vacuo to yield 467 mg (33%) of a crude product, which was purified by flash chromatography (silica gel, ether), and converted to the HCl salt (white solid) by the addition of 1.1 eq of 1M HCl in ether to free base.

Anal. Calcd. for $C_{19}H_{21}Cl_2N \cdot 0.5\ H_2O$: C, 66.48; H, 6.46; N, 4.08. Found: C, 66.43; H, 6.48; N, 4.06.

(2RS,3aSR,8bRS)-1,2,3,3a,4,8b-Hexahydro-2-(4-methoxybenzyl)-1-methylindeno[1,2-b]pyrrole Hydrochloride (RTI-4793-46)

o-Allylbenzaldehyde (2.68 g) was suspended in a solution of 46 ml each of toluene and TMEDA in a round-bottom flask equipped with a Dean Stark tube. N-Methyl-p-methoxyphenylalanine hydrochloride (4.25 g) was added, and the solution was heated to reflux for 16 h. After removal of the solvent (in vacuo), 1N HCl was added to the residue, and the pH of the solution was adjusted to 2. Ether was added, and the organic layer was extracted with $H_2O$ (3×50 ml). The combined aqueous layers were basified with ammonium hydroxide and extracted with methylene chloride (3×100 ml). The combined organic layers were dried ($Na_2SO_4$), filtered, and concentrated in vacuo to yield 2.50 g (47% yield) of crude product which was purified by flash chromatography (silica gel, ether), and converted to the HCl salt (yellow solid) by addition of 1.1 eq of 1M HCl in ether to free base.

Anal. Calcd for $C_{20}H_{24}ClNO \cdot H_2O$: C, 69.05; H, 7.53; N, 4.03. Found: C, 69.05; H, 7.30; N, 3.99.

(2RS, 3aSR, 8bRS)-1,2,3, 3a, 4,8b-Hexahydro-2-(3-methanoindole)-1-methylindeno-[1,2-b]pyrrole Hydrochloride (RTI-4793-44)

o-Allylbenzaldehyde (0.344 g) was suspended in a solution of 6 ml each of toluene and TMEDA in a round-bottom flask equipped with a Dean-Stark tube. L-Abrine (0.500 g) was added, and the solution was heated to reflux for 16 hours. After removal of the solvent (in vacuo), 1N HCl was added to the residue, and the pH of the solution was adjusted to 2. Ether was added, and the organic layer was extracted with $H_2O$ (3×50 ml). The combined aqueous layers were basified with ammonium hydroxide and extracted with methylene chloride (3×100 ml). The combined organic layers were dried ($Na_2SO_4$), filtered, and concentrated in vacuo to yield 180 mg (26%) of a product which was purified by flash chromatography (silica gel, ether), and converted to the HCl salt (white solid) by addition of 1.1 eq of 1M HCl in ether to free base.

Anal. Calcd. for $C_{21}H_{23}ClN2.0.5 H_2O$: C, 72.50; H, 6.95; N, 8.05. Found: C, 72.48; H, 6.95; N, 8.05.

Chemical Synthesis of RTI-4793-41 and RTI-4793-48, and Analogs Thereof

Figure 5:
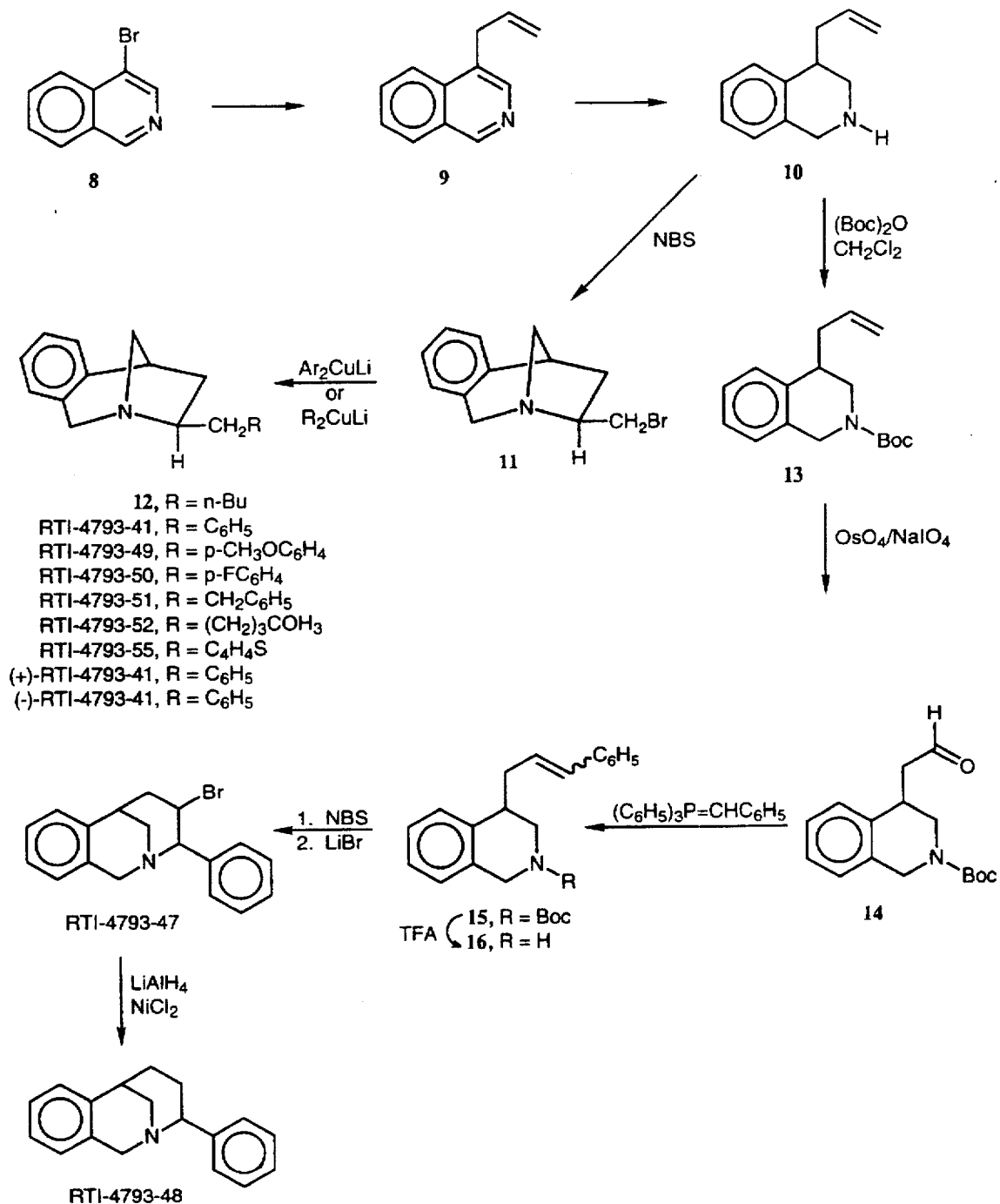
FIG. 5. Schematic diagram for the synthesis of RTI-4793-41 and RTI-4793-48 compounds and analogs thereof.

Compound 12 had been made by coupling 11 with the high order cyano cuprate $Bu_2CNCuLi_2$ (FIG. 5) (Carroll, et al, *J. Chem. Soc., Chem. Commun.*, 9:758–760 (1993)). Coupling 11 with $(C_6H_5)_2CuLi$ gives RTI-4793-41. The route used for the synthesis of RTI-4793-41 and other analogs is also shown in FIG. 5. 3-Bromomethyl-2,3,4,5-tetrahydro-2,5-methano-2-H-2-benzazepine (11) was synthesized following the literature procedure. The bromide 11 was then coupled with the appropriate $R_2CuLi$ to give RTI-4793-41, -49, -50, -51, -52, and -55. The intermediate (+)-10 has been resolved into its (+)- and (−)-isomers using tartaric acid. Subjection of (+)- and (−)-10 to the same reactions as (+)-10 gave (+)-RTI-4793-41 and (−)-RTI-4793-41, respectively.

The syntheses of RTI-4793-47 and RTI-4793-48 are also shown in FIG. 5. Treatment of 10 with di-t-butyl dicarbonate gave the protected amino compound 13. Oxidation with osmium tetroxide/sodium periodate provided the aldehyde 14. Subjection of 14 to a Wittig reaction with the phosphorane prepared from benzyl triphenylphosphonium chloride and butyllithium gave 15 in 93% yield. Removal of the Boc-protecting group with trifluoroacetic acid (TFA) yielded 16. Cyclization with N-bromosuccinimide and isomerization with lithium bromide, yielded RTI-4793-47. Reduction of RTI-4793-47 with lithium aluminum hydride in the presence of nickel chloride gave RTI-4793-48.

A detailed discussion of the synthesis of RTI-4793-41 and RTI-4793-48, and analogs thereof is presented below.

RTI-4793-41

To a suspension of $CuBr.Me_2S$ (1.26 g, 6.1 mmol) in 1:1 THF:ether (20 ml) at −78° C. under nitrogen was added $C_6H_5Li$ (6.8 ml, 12.2 mmol) dropwise. The suspension was stirred at −78° C. for 1.5 hours. At this time the CuBr was not in solution, so the temperature was increased to 0° C. As the solution warmed, it became homogenous. After 30 minutes at 0° C., the bromide 11 (0.20 g, 0.79 mmol) in 1 :1 THF:ether (20 ml) was added dropwise. The resulting mixture was stirred at 0° C. for 3 hours and then at room temperature for 40 hours. Approximately 60 ml of $NH_4Cl$ (sat) solution was then added and the resulting solution extracted with ether. The combined organic layers were dried over $Na_2SO_4$ and the solvent removed to give 255 mg of crude product. Flash chromatography (95:5 $CH_2Cl_2$/$CH_3OH$) gave 57 mg of pure RTI-4793-41, $R_f$=0.5[7]: mp of HCl salt 124°–128° C.

[1] H NMR. δ1.73 (1H, m), 2.14 (1H, m), 2.58 (1H, m), 2.92–3.38 (4H, br m), 3.32 (1H, m), 3.78 (1H, d, J=17.2 Hz, benzylic methylene), 4.35 (1H, d, J=17.2 Hz, benzylic methylene), and 6.92–7.29 (9H, br m, ArH).

$^{13}C$ NMR. δ40.4, 43.1, 44.9, 60.9, 66.0, 125.9, 126.0, 126.3, 126.5, 126.6, 128.2 (2C), 129.0 (2C), 133.2, 140.0, and 143.2.

MS. m/e 249 (M+$C_{18}H_{19}N$, 100%).

Anal. Calcd. for $C_{18}H_{20}ClN.H_2O$: C, 71.16; H, 7.30; N, 4.61. Found: C, 71.08; H, 7.25; N, 4.58.

RTI-4793-49

4-Bromoanisole (1.87 g, 10 mmol) was dissolved in 50 ml ether and cooled to −78° C. t-BuLi 30 (11.8 ml, 20 mmol) was added dropwise. After stirring for 1 hour at this temperature, the mix was allowed to warm to room temperature and stirred for 30 min.

To a suspension of $CuBr.Me_2S$ (1.29 g, 6.2 mmol) in THF (30 ml) at −78° C. under nitrogen, the ArLi from above was added via a cannula. The mixture was allowed to warm to −40° C. and stirred for 1 hour. The bromide 11 (0.312 g, 1.24 mmol) in THF (20 ml) was added dropwise. The resulting mixture was stirred at −40° C. for 2 hours and then at room temperature for 49 hours. Approximately 100 ml of 10% $NH_4OH$ (conc.)/$NH_4Cl$ (sat.) solution was then added and the resulting solution extracted with ether. The combined organic layers were dried over $Na_2SO_4$ and the solvent removed to give the crude product. Flash chromatography (97:3 to 90:10 $CH_2Cl_2$/2-propanol) gave 250 mg (72% yield) of pure RTI-4793-49.

$^1H$ NMR. δ1.71 (1H, m), 2.07 (1H, dd, J=12.4, 7.6, and 2.1 Hz), 2.53 (1H, dd, J=13.8, 5.8 Hz), 2.91–3.03 (4H, m), 3.28 (1H, m), 3.75 (3H, OMe), 3.80 (1H, d, J=17.1 Hz, benzylic methylene), 4.35 (1H, d, J=17.1 Hz, benzylic methylene), 6.73–7.15 (8H, br m, ArH).

$^{13}C$ NMR. 6 40.4, 42.1, 44.8, 54.7, 55.2, 60.9, 66.3, 113.7 (2C), 126.1, 126.4, 126.6, 126.7, 130.0 (2C), 132.0, 133.1, 143.1 and 158.0.

Anal. Calcd. for $C_{19}H_{22}ClNO.0.5H_2O$: C, 70.25; H, 7.14; N, 4.31. Found: C, 70.05; H, 7.18; N, 4.28.

RTI-4793-50

1-Bromo-4-fluorobenzene (1.56 9, 8.91 mmol) was dissolved in 50 ml ether and cooled to −78° C. t-BuLi (11.0 ml, 17.7 mmol) was added dropwise. After stirring for 1 hour at this temperature, the mix was allowed to warm to room temperature and stirred for 30 min.

To a suspension of $CuBr.Me_2S$ (0.913 g, 4.4 mmol) in THF (30 ml) at −78° C. under nitrogen, the ArLi from above was added via a cannula. The mixture was allowed to warm to −40° C. and stirred for 1 hour. The bromide 11 (0.280 g, 1.11 mmol) in THF (20 ml) was added dropwise. The resulting mixture was stirred at −40° C. for 2 hours and then at room temperature for 20 hours. Approximately 100 ml of 10% $NH_4OH$ (conc.)/$NH_4Cl$ (sat.) solution was then added and the resulting solution extracted with ether. The combined organic layers were dried over $Na_2SO_4$ and the solvent removed to give the crude product. Flash chromatography (95:5 $CH_2Cl_2$/2-propanol) gave 274 mg (82% yield) of pure RTI-4793-50.

$^1H$ NMR. δ1.68 (1H, m), 2.09 (1H, ddd, J=12.3, 7.7, and 1.6Hz), 2.54 (1H, dd, J=13.8 and 7.4 Hz), 2.87–3.10 (3H, m), 2.91 (1H, dd, 13.8 and 7.4 Hz), 3.25 (1H, m), 3.72 (1H, d, J=17.2 Hz, benzylic methylene), 4.33 (1H, d, J=17.2 Hz, benzylic methylene), and 6.89–7.47 (8H, m, ArH).

Anal. Calcd. for $C_{18}H_{19}ClFN$: C, 71.16; H, 6.30; N, 4.61. Found: C, 70.97; H, 6.33; N, 4.52.

RTI-4793-51

$(C_6H_5)_3Sn(CH_2C_6H_5)$ (5.3 g, 12 mmol) was dissolved in 14 ml ether and cooled to −78° C. $C_6H_5Li$ (6.7 ml, 12 mmol) was added dropwise. After stirring for 1 hour at this temperature, the mixture was allowed to warm to room temperature and stir for 30 minutes.

To a suspension of CuBr·Me$_2$S (1.7 g, 8.3 mmol) in THF (30 ml) at −78° C. under nitrogen was added C$_6$H$_5$CH$_2$Li from the above via a syringe (16 gauge needle used to transfer entire suspension of lithium reagent). The mixture was allowed to warm to −40° C. and stirred for 1 hour. The bromide 11 (0.376 g, 1.66 mmol) in THF (30 ml) was added dropwise. The resulting mixture was stirred at −40° C. for 2 hours and then at room temperature for 15.5 hours. Approximately 40 ml of 10% NH$_4$OH (conc.)/NH$_4$Cl (sat.) solution was then added and the resulting solution extracted with ether. The combined organic layers were dried over Na$_2$SO$_4$ and the solvent removed to give the crude product. Flash chromatography (95:5 CH$_2$Cl$_2$/CH$_3$OH) gave 344 mg (79% yield) of pure RTI-4793-51.

$^1$H NMR. δ1.58–1.89 (3H, m), 2.16–2.21 (1H, m), 2.63–3.16 (6H, m), 3.77 (1H, d, J=17.2 Hz, benzylic methylene), 4.40 (1H, d, J=17.2 Hz, benzylic methylene), and 6.93–7.37 (9H, br m, ArH).

$^{13}$C NMR. δ33.9, 38.9, 40.2, 45.2, 54.6, 64.5, 125.7, 126.1, 126.4, 126.6, 126.7, 128.4 (2C), 128.5 (2C), 133.2, 142.3, and 143.2.

Anal. calcd. for C$_9$H$_{22}$ClN·0.25 H$_2$O: C, 74.98; H, 7.45; N, 4.60. Found: C, 74.88; H, 7.33, N, 4.59.

RTI-4793-52

1-Bromo-3-phenylpropane (1.83 g, 9.2 mmol) was dissolved in 50 ml ether and cooled to −78° C. t-BuLi (10.8 ml, 18.4 mmol) was added dropwise. After stirring for 1 hour at this temperature, the mix was allowed to warm to room temperature, and stirred for 30 minutes. To a suspension of CuBr·Me$_2$S (1.1 g, 5.4 mmol) in THF (30 ml) at −78° C. under nitrogen the RLi from above was added via a cannula. The mixture was allowed to warm to −40° C. and stirred for 30 minutes, and cooled to −78°C. The bromide 11 (0.289 g, 1.15 mmol) in THF (20 ml) was added dropwise, and the resulting solution was warmed to −40° C. The resulting mixture was stirred at −40° C. for 1.5 hours and then at room temperature for 4 hours. Approximately 100 ml of 10% NH$_4$OH (conc.)/NH$_4$Cl (sat.) solution and ether (50 ml) were then added and the resulting solution extracted with ether. The combined organic layers were dried over Na$_2$SO$_4$ and the solvent removed to give the crude product. Flash chromatography (98:2 to 95:5 CH$_2$Cl$_2$/2-propanol) gave 222 mg (66% yield) of RTI-4793-52.

$^1$H NMR. δ1.32–1.16 (7H, m), 2.14–2.23 (1H, m), 2.61 (2H, t, J=7.3), 2.93–3.08 (4H, m), 3.78 (1H, d, J=17.1 Hz, benzylic methylene), 4.40 (1H, d, J=17.1 Hz, benzylic methylene), and 6.85–7.44 (9H, br m, ArH).

$^{13}$C NMR. S 27.2, 31.6, 36.0, 36.9, 40.1, 45.0, 54.6, 60.8, 65.3, 125.7, 126.3, 126.5, 126.8 (2C), 128.3, 128.4 (2C), 132.6, 133.1, 142.7 and 142.8.

Anal. Calcd. for C$_{21}$H$_{26}$ClN·H$_2$O: C, 72.92; H, 8.16; N, 4.05. Found: C, 73.20; H, 7.76; N, 4.01.

RTI-4793-55

Thiophene (1.13 g, 13.4 mmol) was dissolved in Et$_2$O (40 ml). To this solution was added n-BuLi (5.2 ml, 13.0 mmol, 2.5M) dropwise. After 30 minutes, the solution was transferred (via cannula) to a suspension of CuBr·Me$_2$S (1.55 g, 7.5 mmol) in THF (30 ml) at −45° C. The mixture was stirred at −45° C. for 1 hour. Compound 11 (0.348 g,1.38 mmol) in THF (20 ml) was added dropwise. The resulting mixture was stirred at −45° C. for 3 hours and then at room temperature overnight. Approximately 100 ml of NH$_4$OH (conc.)/NH$_4$Cl (sat.) (1:9) solution and 50 ml of Et$_2$O were then added and the resulting solution stirred vigorously for 1 hour. The layers were separated, and the aqueous layer was extracted with ether (3×50 ml). The combined organic layers were evaporated. The residue was dissolved in 50 ml of Et$_2$O and extracted with 3M HCl (3× 25 ml). The combined aqueous layers were basified with 3M NaOH and extracted with methylene chloride. The combined organic layers were dried over Na$_2$SO$_4$ and the solvent removed. Flash chromatography (95:5 CH$_2$Cl$_2$/MeOH) gave RTI-4793-55 (52 mg) as an oil: mp of HCl salt 45° C. (dec).

$^1$H NMR (free base). δ 1.75 (1H, m), 2.23 (1H, m), 2.85 (1H, dd, J=14.7 and 6.4 Hz), 3.00–3.24 (4H, br m), 3.30 (1H, m), 3.84 (1H, d, J=17.2 Hz, benzylic methylene), 4.39 (1H, d, J=17.3 Hz, benzylic methylene) and 6.82–7.24 (7H, br m, ArH).

$^{13}$C NMR. δ37.4, 40.5, 45.0, 54.7, 60.8, 66.2, 123.7, 124.9, 126.1, 126.4, 126.65 (2C), 126.7, 133.3, 143.0, and 143.1.

Anal. Calcd. for C$_{16}$H$_{18}$ClNS·H$_2$O: C, 62.02; H, 6.51; N, 4.52. Found: C, 61.79; H, 6.35; N, 4.45.

(−)-RTI-4793-41

A. (−)-Compound 10. Compound 10 (2.99 g, 17.26 mmol) was dissolved in 17 ml of EtOH (95%). To this was added L-tartaric acid (2.59 g,17.26 mmol) dissolved in 17 ml of EtOH (95%). The salt that formed was isolated and recrystallized twice from EtOH (95%). The salt was dried at 500C at high vacuum to give 1.37 g (4.24 mmol) of the salt (24.6% yield): mp 133.5°–134° C; $[\alpha]^{20}_D$ −26.1 (c 0.925, MeOH).

Anal. Calcd. for C$_{16}$H$_{21}$NO$_6$: C, 59.43; H, 6.55; N, 4.30. Found: C, 59.44; H, 6.54; N, 4.30.

To the salt was added 1N NaOH/brine (50:50), and the mixture was extracted exhaustively with methylene chloride. The combined organic layers were washed with brine, dried over Na$_2$SO$_4$, and the solvent removed to give pure (−)-10 (0.661 9, 3.82 mmol, 22.1%) as an oil: $[\alpha]_D$ −25.1 (c 0.975, CHCl$_3$).

$^1$H NMR (free base). δ 1.87 (1H, br m), 2.37–2.50 (2H, m), 2.70–2.85 (1H, m), 2.99–3.14 (2H, m), 3.98 (2H, br s), 5.03–5.14 (2H, m, alkene methylene), 5.75–5.89 (1H, m, alkene methine) and 6.98–7.22 (4H, m, ArH).

B. (−)-Compound 11. (−)-Compound 10 from above (0.430 g, 2.48 mmol) was dissolved in methylene chloride (20 ml) and cooled to 0° C. To this was added NBS (0.459 g, 2.58 mmol) as a solid. The mixture was allowed to stir for 3 hours at this temperature and then was stirred in the freezer overnight. NaOH (0.5N) was added, and the mixture was extracted with methylene chloride (3×40 ml). The combined organic layers were washed with brine and dried over Na$_2$SO$_4$. Flash chromatography with Et$_2$O/hexane/NEt$_3$ (50:50:1) gave (−)-11 (0.534 g, 2.12 mmol, 85.5%) as an oil: $[\alpha]^{20}_D$ −57.2 (c 0.930, CHCl$_3$).

$^1$H NMR (free base). δ1.75–1.85 (1H, m), 2.28–2.36 (1H, m), 2.98–3.13 (3H, m), 3.25–3.41 (2H, m), 3.47–3.53 (1H, m), 3.78 (1H, d, J=17.2 Hz, benzylic methylene), 4.40 (1H, d, J=17.2 Hz, benzylic methylene) and 6.95–7.20 (4H, m, ArH).

C. (−)-RTI-4793-41. To a suspension of CuBr·Me$_2$S (1.28 g, 6.23 mmol) in THF (90 ml) at −45° C. under nitrogen was added C$_6$H$_5$Li (6.8 ml,12.2 mmol) dropwise. The suspension was stirred at −45° C. for 1.0 hour. (−)-Compound 11 (0.388 g, 1.54 mmol) in THF (30 ml) was added dropwise. The resulting mixture was stirred at −45° C. for 3 hours and then at room temperature overnight. Approximately 100 ml of NH$_4$OH (conc.)/NH$_4$Cl (sat.) (1:9) solution and 50 ml of Et$_2$O were then added and the resulting solution stirred vigorously for 1 hour. The layers were separated, and the aqueous layer was extracted with ether (3×50 ml). The combined organic layers were evaporated. The residue was dissolved in 50 ml of Et$_2$O and extracted with 3M HCl (3×25 ml). The combined aqueous layers were basified with 3N NaOH and extracted with methylene chloride. The combined organic layers were dried over $Na_2SO_4$ and the solvent removed. Flash chromatography (95:5 $CH_2Cl_2$/iPrOH) gave (−)-RTI-4793-41 (173 mg, 0.69 mmol, 45%) as an oil: $[\alpha]^{20}_D$ −4.49 (c 0.98, $CHCl_3$).

Melting point of HCl salt 231° C. (dec.). Rotation of HCl salt $[\alpha]^{20}_D$ −0.92 (c 1.31, $CHCl_3$).

$^1H$ NMR (free base). δ1.73 (1H, m), 2.14 (1H, m), 2.58 (1H, m), 2.92–3.38 (4H, br m), 3.32 (1H, m), 3.78 (1H, d, J=17.2 Hz, benzylic methylene), 4.35 (1H, d, J=17.2 Hz, benzylic methylene) and 6.92–7.29 (9H, br m, ArH).

$^{13}C$ NMR. 40.4, 43.1, 44.9, 54.7, 60.9, 66.0, 125.9, 126.0, 126.3, 126.5, 126.6, 128.2 (2C), 129.0 (2C), 133.2, 140.0 and 143.2.

Anal. Calcd. for $C_{18}H_{20}ClN \cdot 0.33 H_2O$: C, 74.09; H, 7.14; N, 4.80. Found: C, 74.05; H, 7.08; N, 4.83.

(+)-RTI-4793–41

A. (+)-Compound-10. The mother liquor from the isolation of the (−)-3/L-tartaric acid salt was neutralized with 1N NaOH, and the free base was extracted with $CH_2Cl_2$. The $CH_2Cl_2$ layer was dried over $Na_2SO_4$ and the solvent removed to give 1.75 g of an oil. The oil was dissolved in 8 ml of EtOH (95%). To this was added D-tartaric acid (1.29 g, 8.63 mmol) dissolved in 8 ml of EtOH (95%). The salt that formed was isolated and recrystallized twice from EtOH (95%). The salt was dried at 50° C. at high vacuum to give 1.34 g (4.14 mmol) of the salt (24.0% yield): mp 133.5°–134° C., $[\alpha]^{20}_D$ +24.1 (c 0.920, MeOH).

Anal. Calcd. for $C_{16}H_{21}NO_6$: C, 59.43; H, 6.55; N,4.30. Found: C, 59.22; H, 6.57; N, 4.30.

To the salt was added 1N NaOH/brine (50:50), and the mixture was extracted exhaustively with methylene chloride. The combined organic layers were washed with brine, dried over $Na_2SO_4$, and the solvent was removed to give pure (+)-1O (0.670 g, 3.90 mmol, 22.6%) as an oil: $[\alpha]^{20}_D$+ 25.1 (c 1.53, $CHCl_3$).

B. (+)-Compound-11. Compound (+)-10from above (0.600 g, 3.46 mmol) was dissolved in methylene chloride (30 ml) and cooled to 0° C. To this was added NBS (0.641 g, 3.6 mmol) as a solid. The mixture was allowed to stir for 3 hours at this temperature and then was stirred in the freezer overnight. NaOH 0.5N was added, and the mixture was extracted with methylene chloride (3×40 ml). The combined organic layers were washed with brine and dried over $Na_2SO_4$. Flash chromatography with $Et_2O$/hexane/$NEt_3$ (50:50:1) gave (+)-11 (0.678 g, 2.69 mmol, 77.8%) as an oil: [a]20D +58.3 (c 1.02, $CHCl_3$). The $^1H$ NMR spectrum was identical to the spectrum of (−)-11.

C. (+)-RTI-4793-41. To a suspension of $CuBr \cdot Me_2S$ (2.75 g, 13.4 mmol) in THF (150 ml) at −45° C. under nitrogen was added $C_6H_5Li$ (14.9 ml, 26.8 mmol) dropwise. The suspension was stirred at −45° C. for 1 hour. Compound (+)-11 (0.490 g, 1.95 mmol) in THF (20 ml) was added dropwise. The resulting mixture was stirred at −45° C. for 3 hours and then at room temperature overnight. Approximately 100 ml of $NH_4OH$ (conc.)/$NH_4Cl$ (sat.) (1:9) solution and 50 ml of $Et_2O$ were then added and the resulting solution stirred vigorously for 1 hour. The layers were separated, and the aqueous layer was extracted with ether (3×50 ml). The combined organic layers were evaporated. The residue was dissolved in 50 ml of $Et_2O$ and extracted with 3M HCl (3×25 ml). The combined aqueous layers were basified with 3M NaOH and extracted with methylene chloride. The combined organic layers were dried over $Na_2SO_4$ and the solvent removed. Flash chromatography (95:5 $CH_2Cl_2$/i-PrOH) gave (+)-RTI-4793-41 (242 mg, 0.971 mmol, 50%) as an oil: $[\alpha]^{20}_D$+4.62 (c 0.93, $CHCl_3$).

Melting point of HCl salt 230° C. (dec.). Rotation of HCl salt $[a]^{20}D$+0.94 (c 1.27, $CHCl_3$).

$^1H$ NMR (free base). δ1.73 (1H, m), 2.14 (1H, m), 2.58 (1H, m), 2.92–3.38 (4H, br m), 3.32 (1H, m), 3.78 (1H, d, J=17.2 Hz, benzylic methylene), 4.35 (1H, d, J=17.2 Hz, benzylic methylene) and 6.92–7.29 (9H, br m, ArH).

$^{13}C$ NMR. 40.4, 43.1, 44.9, 54.7, 60.9, 66.0, 125.9, 126.0, 126.3, 126.5, 126.6, 128.2 (2C), 129.0 (2C), 133.2, 140.0 and 143.2.

Anal. Calcd. for $C_{18}H_{20}ClN \cdot 0.33 H_2O$: C, 74.09; H, 7.14; N, 4.80. Found: C, 73.85; H, 6.98; N, 4.74.

Compound 13

To 10 (5.07 g, 29.3 mmol) dissolved in $CH_2Cl_2$ (30 ml) was added di-tert-butyl dicarbonate (7.7 g, 35.2 mmol), and the mixture was stirred for 2 hours (TCL: ether on $SiO_2$ plates). 2-Diethylaminoethylamine (848 mg, 7.3 mmol) was added and the mixture was stirred for 15 minutes. $CH_2Cl_2$ (25 ml) and 1M $KHSO_4$ (25 ml) were added and the layers separated. The organic layer was washed with 1M $KHSO_4$ (4×20 ml), water (1×20 ml), brine (3×20 ml), and dried over $MgSO_4$. Removal of the solvent gave 13 (7.22 g, 26.4 mmol, 90%) as an oil.

1 H NMR. δ1.50 (9H, s, tert-butyl), 2.32 (2H, t, J=8.4 Hz), 2.83 (1H, br s), 4.02 (1H, br m), 3.25 (1H, br m), 4.80 (1H, br m), 4.34 (1H, br m), 5.07–5.13 (2H, m, alkene methylene), 5.81–5.98 (1H, m, alkene methine), and 7.10–7.20 (4H, m, ArH).

Compound 14

To carbamate 6 (3.62 g, 13.3 mmol) dissolved in 200 ml THF/$H_2O$ (4:1) was added ° $S^O4$ (1.5 ml, 5% solution in tert-butanol). After 5 minutes $NaIO_4$ (10 g, 46.8 mmol) was added over 10 minutes in three batches. The mixture was allowed to stir for 30 hours. $Et_2O$ (100 ml) and $H_2O$ (100 ml) were added, and the ether layer was washed with $H_2O$ (2×100 ml) and then with brine (50 ml). The combined organic layer was dried over $MgSO_4$ and the solvents removed. The crude material was purified by flash chromatography (hexane/i-propanol, 90:10) to give 14 (2.95 g, 10.7 mmol, 81%) as a brown oil.

$^1H$ NMR. δ1.48 (9H, s, tert-butyl), 2.61 (1H, dd, J=18.0 and 4.4 Hz), 2.80 (1H, dd, J=18.0 and 9.0 Hz), 3.22 (1H, br d, J=12.8Hz), 3.42 (1H, br s), 4.10 (1H, dd, J=13.4 and 2.5 Hz), 5.00 (1H, br m), 4.29 (1H, br m), 7.07–7.30 (4H, m, ArH) and 9.80 (1H, s, aldehyde methine).

Compounds 15 and 16

Benzyl triphenylphosphonium chloride (0.613 g, 1.58 mmol) was dissolved in dry THF (4 ml), and butyllithium (1 ml, 1.47 mmol) was added dropwise to produce a dark red solution. The mixture stirred for 30 minutes and was then cooled to −40° C. The aldehyde 14 (370 mg, 1.3 mmol) dissolved in dry THF (1 ml) was added, and the temperature was allowed to warm to room temperature (over ca. 1 hour) and stirred for 3 hours. Ammonium chloride (50 ml sat. solution) was added and the mixture stirred overnight. $H_2O$ (25 ml) was added and aqueous layer was washed with $H_2O$ (3×20 ml). Combined organic layers washed with $H_2O$ (2×20 ml), brine (2×20 ml) and dried over $Na_2SO_4$. Removal of the solvents gave the product contaminated with a large amount of triphenyphosphineoxide. Flash chromatography (hexane/$Et_2O$, 8:1) gave cis and trans 15 (420 mg, 93%) as a clear oil.

The Boc protected amine 15 from above (420 mg, 1.2 mmol) was dissolved in 9 ml of $CH_2Cl_2$/TFA (2:1 v/v) and stirred for 15 minutes at room temperature. 4N NaOH was added until the pH reached 10. The aqueous layer was extracted with $CH_2Cl_2$ (4×20 ml), and the combined organic layers were dried over $Na_2SO_4$. After removal of the solvent, flash chromatography (hexane/i-propanol/NEt$_3$, 50:50:1) gave 16 (244 mg, 81%) as an oil.

$^1$H NMR. δ1.81 (1H, NH), 2.54–3.13 (5H, m), 4.00 (br s), 3.95 (br s), 5.68–5.78 (alkene), 6.18–6.30 (alkene), 6.42–6.55 (alkene) and 7.01–7.33 (9H, m, ArH).

RTI-4793–47

Alkene 16 (0.760 g, 3.05 mmol) was dissolved in 20 ml THF at 0° C. NBS (0.55 9, 3.09 mmol) was added as a solid and the resulting mixture was stored in the refrigerator over night. The mixture was diluted with 1N NaOH and extracted with ether. Combined organic extracts were dried over Na$_2$SO$_4$ and the volatiles removed. The crude material was dissolved in 15 ml of reagent grade acetone, two small spatulas of LiBr were added, and the mixture was stirred over the weekend. Water was added, and the mixture was extracted with ether. The combined organic extracts were dried over Na$_2$SO$_4$, and the volatiles ere removed. Flash chromatography over SiO$_2$ (1:1 hexane/ether) gave 343 mg (34%) of RTI-4793-47.

$^1$H NMR. δ2.45–2.66 (2H, m), 2.90 (1H, br m), 3.38–3.55 (2H, m), 3.75 (2H, m), 4.25 (2H, m), and 6.90–7.54 (9H, m, ArH).

$^{13}$C NMR. 5 35.9, 45.3, 46.4, 47.7, 53.8, 72.3, 124.9, 126.6, 127.7, 128.2 (2C), 128.4, 129.2 (2C), 137.0, 137.8, and 138.5. Note: There was one coincidental overlap.

Anal. Calcd. for C$_{18}$H$_{19}$BrClN: C, 59.28; H, 5.25; N, 3.84. Found: C, 59.12; H, 5.28; N, 3.76.

RTI-4793–48

The bromide RTI-4793-47 (0.074 g, 0.226 mmol) dissolved in 2 ml dry THF was added to NiCl$_2$ (0.035 g, 0.270 mmol weighed out in a glove bag) at −78° C. To this mixture was added LAH (0.27 ml, 0.270 mmol), and the resulting black mixture was stirred for 25 hours. 0.5N NaOH (2 ml) was added followed by Na/K tartrate (sat. soln.) and the mixture stirred overnight. The solution was extracted with methylene chloride. Combined organic layers washed with brine and dried over Na$_2$SO$_4$. Volatiles were removed to give 53 mg (94%) of crude product. Flash chromatography (ether) gave 42 mg (75%) of pure RTI-4793-48.

$^1$H NMR. δ1.57–1.67 (2H, m), 1.89–2.13 (2H, m), 2.77 (1H, br m), 3.33–3.49 (2H, m), 3.58 (1H, d, J=18.2), 3.89 (1H, d, J=18.2), 4.12 (1H, dd, J=10.7 and 5.7 Hz), and 6.83–7.48 (9H, m, ArH).

$^{13}$C NMR. δ21.2, 31.4, 33.1, 47.9, 54.2, 65.0, 124.8, 125.8, 125.9, 127.0, 128.16 (2C), 128.2 (2C), 138.4, 139.7, and 142.4.

Anal. Calcd. for C$_{18}$H$_{20}$NCl$_2$: C, 67.08; H, 6.57; N, 4.35. Found: C, 67.54; H, 6.45; N, 4.28.

Preparation of Membranes

Large batches of frozen membranes were prepared with minor modifications of published procedures (Rothman, et al. (1989), supra). Twenty to thirty frozen guinea pig brains with cerebellum were thawed for 15 minutes and homogenized with a Polytron in ice-cold 5 mM Tris-HCl, pH 8.0 (10 ml/brain). The homogenate was centrifuged at 37,000×g for 10 minutes, and the pellet was washed by resuspension in the same volume of buffer followed by recentrifugation. The pellets were resuspended in an equal volume of 5 mM Tris-HCl, pH 8.0, and the concentration was adjusted to 50 mM by the addition of 1M Tris-HCl, pH 8.0. The homogenate was centrifuged for 10 min at 37,000×g. The pellets were then washed three times by resuspension and centrifugation using 50 mM Tris-HCl, pH 8.0. The final pellets were resuspended in the Tris-HCl buffer (0.5 ml/brain), pooled and 1 ml aliquots were distributed to microfuge tubes, which were stored at −70° for assay.

Membranes for the [$^3$H]nisoxetine assay were prepared as described (Rothman, R. B., et al. Synapse 14: 34–39 (1993)).

For [$^3$H]J2B-carbomethoxy-3B-(4-fluorophenyl)-tropane (CFT, WIN35,428) binding assays, male Sprague-Dawley rats (200 to 300 gm) were anesthetized with CO$_2$ gas, and decapitated. Striata were dissected using glass manipulators, placed in small plastic containers, and then allowed to freeze by placing the container in dry ice.

Striata collected in this way were stored at −1350° C. On the day of the assay, each striatum was placed in ice-cold binding buffer (BB: 55.2 mM sodium phosphate buffer, pH 7.4, 5 ml per caudate), and homogenized while still frozen with a Polytron. The homogenate was centrifuged for 10 min at 30,000×g, and the pellet was resuspended in an equal volume of BB. The homogenate was recentrifuged, and the pellet was resuspended in an equal volume of BB. An aliquot was saved for determination of protein (0.5 ml), and the remaining homogenate was brought up to a final volume of 22 ml/striatum using ice-cold BB. Typical final protein concentrations, determined with the Lowry method (Lowry, O. H., et al. J. Biol. Chem. 193: 265–275 (1951)), were 100 µg/ml. Initial experiments showed that at these protein concentrations, the specific binding was directly proportional to protein concentration, and that less than 10% of the radioligand was bound (data not shown). Aliquots of membranes were then used in the radioligand binding assays.

Binding Assays

The [$^3$H]TCP binding assay for PCP site 2 was conducted with minor modifications of published protocols (Rothman, et al. (1989), supra). Briefly, 12×75 mm polystyrene test tubes were prefilled with 100 µl of [$^3$H]TCP (2 nM final concentration) in a protease inhibitor cocktail (PIC) containing 5000 nM (+) -MK801, 100 µl of distilled H$_2$O or drug (in distilled H$_2$O), 50 µl of buffer (5 mM Tris-HCL, pH 8.0), and 750 µl of membrane (0.5–1.0 mg/ml protein, in 5 mM Tris-HCl, pH 8.0). The (+)-MK801 (500 nM final concentration) was included to block [$^3$H]TCP binding to PCP site 1. The protease inhibitor cocktail was composed of 25 µg/ml leupeptin, 25 µg/ml chymostatin, 0.1 mM EDTA, and 0.1 mM ethylene glycol-bis-(beta-aminoethyl-ether)-N, N,N',N'-tetraacetic acid (EGTA). The incubation time was 18–24 hours at 4° C. (steady state) in a final volume of 1 ml. Triplicate samples were filtered with an MR24 Brandel Cell Harvester and washed with two 5 ml aliquots of ice cold buffer. Whatman GF/B filters were presoaked in buffer containing 2% polyethylenimine. The tritium retained on the filters was measured using a Taurus scintillation counter at 44% efficiency after an overnight extraction into ICN Cytoscint cocktail. Non specific binding was determined using 10 µM of TCP. Protein was determine using the method of Lowry, et al., supra. The [ H](+)-MK8O1 assay (2 µM final concentration) proceeded as described above for [$^3$H]TCP except that (+)-MK801 was not included as a blocker, the time was for 4–6 hours at 4° C., and nonspecific binding was determined with 1 µM TCP.

The [$^3$H]nisoxetine assay for the norepinephrine transporter (NE) was carried out as described (Rothman, et al. (1993), supra; Tejani-Butt, S. M., et al. Eur. J. Pharmacol. 191:239–243 (1990)). DA transporters were labeled with [$^3$H)CFT with minor modifications of published protocols (Madras, B. K., et al. Mol. Pharmacol. 36: 518–524 (1989)). Briefly, 12×75 mm polystyrene test tubes were prefilled with 100 µl of drug, 100 µl of radiolabeled (1 nM final concentration), 50 µl of buffer. Drugs were dissolved in BB containing 1 mg/ml bovine serum albumin (BB/BSA). Radioligands were made to a final concentration in a protease inhibitor cocktail containing 1 mg/ml BSA {BB containing chymostatin (25 µg/ml), leupeptin (25 µg/ml), EDTA (100 µM), and EGTA (100 µM)}. The assay was initiated by the addition of 750 μl of membranes, prepared as described above. Brandel cell harvesters were used to filter the samples over Whatman GF/B filters, which were presoaked in wash buffer (ice-cold 10 mM TRIS-HCL, pH 7.4 containing 150 mM NaCl) containing 2% polyethylenimine. In this procedure, samples were filtered and then washed with two 4 ml aliquots of ice-cold wash buffer. Nonspecific binding was defined using 10 μM (final concentration) GBR12909. All subsequent steps were identical to those described above.

Biogenic Amine Uptake Assays

Synaptosomal uptake assays were carried out as described (Rothman et al. (1993), supra). Briefly, synaptosomes were prepared by homogenization of rat striatum (for [$^3$H]DA reuptake) or whole rat brain minus cerebellum (for [$^3$H]5-HT reuptake) in ice-cold 10% sucrose, using a Potter-Elvehjem homogenizer. After a 1000×g centrifugation for 10 min at 4° C., the supernatants were retained on ice. The uptake assays were initiated by the addition of 100 μl of synaptosomes to 12×75 mm polystyrene test tubes, which were prefilled with 750 μl of [$^3$H]ligand (2 nM [$^3$H]5-HT or 5 nM [$^3$H]DA) in a Krebs-phosphate buffer (pH 7.4), which contained ascorbic acid (1 mg/ml) and pargyline (50 μM) (buffer), 100 μl of test drugs made up in buffer containing 1 mg/ml bovine serum albumin, and 50 μl of buffer. The [$^3$H]5-HT reuptake experiments were conducted in the presence of 100 nM nomifensine and 100 μM GBR12935 in order to block any possible reuptake into NE and DA nerve terminals. Although these agents were routinely included in the [$^3$H]5-HT reuptake assays, control studies showed that they had no discernible effect on [3H]5-HT reuptake (data not shown). The nonspecific uptake of each [$^3$H]ligand was measured by incubations in the presence of 1 μM GBR12909 ([$^3$H]DA) and 10 μM fluoxetine ([$^3$H]5-HT). The incubations were terminated after a 15 min ([$^3$H]DA) or 30 min ([$^3$H]5-HT) incubation at 25° C. by adding 4 ml of wash buffer (10 mM TRIS-HCl, pH 7.4 containing 0.9% NaCl at 25° C.), followed by rapid filtration over Whatman GF/B filters and one additional wash cycle. Control studies indicated that specific uptake was (1) linear with time up to 30 min; and (2) was directly proportional to protein in the protein range used here. The Krebs-phosphate buffer contained 154.5 mM NaCl, 2.9 mM KCl, 1.1 mM CaCl$_2$, 0.83 mM MgCl$_2$ and 5 mM glucose. The tritium retained on the filters was counted, in a Taurus beta counter, after an overnight extraction into ICN Cytoscint cocktail.

Electrophysiological Studies

Whole-cell recordings of NMDA-induced currents in cultured rat hippocampal neurons were carried out as described previously (Subramaniam, S., et al. *Neurosci. Lett.* 147: 213–216 (1992)). Hippocampal neurons grown in primary culture from 19-day-old Sprague-Dawley rat embryos were used 7–14 days after plating. The extracellular recording solution consisted of (in mM): 140 NaCl, 5 KCl, 0.1 CaCl$_2$, and 10 HEPES (osmolality, 315–325 mOsm; pH, 7.4). Tetrodotoxin (1 μM) and strychnine (1 μM) were added to block Na+channel currents and glycine-activated Cl$^-$ currents, respectively. Patch pipettes (2–5 MΩ) were prepared from filament-containing thin wall glass capillary tubes and filled with an intracellular solution that consisted of (in mM): 145 CsCl, 2 MgCl$_2$, 5 HEPES, 0.1 CaCl$_2$, and 1 EGTA (osmolality, 310 mOsm; pH, 7.4). Drugs were dissolved in recording solution and applied via a rapid gravity-fed perfusion system. Flow of the drug solutions was regulated by a microvalve operated by a programmable controller. Whole-cell recordings were performed with an Axopatch 1c patch-clamp amplifier (Axon Instruments, Burlingame, Calif.) and displayed on a high speed ink pen recorder (Gould Electronics, Cleveland, Ohio).

In Vivo Microdialysis Experiments

Male Sprague Dawley rats (350–450 g) were anesthetized with chloral hydrate (400 mg/kg; 100 mg/ml) and supplemented as required (90 mg/kg) to abolish the corneal reflex. Animals were then placed in a stereotaxic frame and dialysis probes (CMA 12, 2 mm) were implanted into the nucleus accumbens (AP:+2mm, LAT:+1.5mm, H:-7.5mm relative to bregma) according to the atlas of Paxinos and Watson (Paxinos, G. "The rat brain in stereotaxic coordinates." (New York: Academic Press, 1982)). The dialysis probes were perfused with a physiological medium containing 145 mM NaCl, 4 mM KCl, 1.3 mM CaCl$_2$, and 2 mM Na$_2$HPO$_{41}$ the final pH of the medium being pH 7.4. The probes were dialyzed at a flow rate of 2.34 ml/min. and samples were collected every 15 min.

The dialysis probes were allowed to equilibrate for 1–2 hours prior to collection of the baseline samples. Baseline samples were then collected until three consecutive samples did not differ significantly. RTI-4793-14 (1–100 μM) was then administered focally via the dialysis probe for a 15 min. sampling period at the end of which normal dialysis medium was dialyzed through the probe. Sampling continued for a further 3 samples before application of the subsequent concentration of RTI-4793-14. In a subsequent group of animals RTI-4793-14 was administered systemically (5mg/kg; 5mg/ml) via a femoral vein catheter.

The samples were analyzed for DA using HPLC with electrochemical detection. The mobile phase (75 mM NaH$_2$PO$_4$, 1.5 mM sodium dodecyl sulphate, 20 mM EDTA, 15% acetonitrile and 12% methanol, pH 5.6) was filtered and degassed before pumping at a rate of 0.75 ml/min. through a HR-80 column (3m BDS, 80×4.6 mm). Electrochemical detection-was performed using a Coulochem II with Guard cell:+350 mV, Det 1: −75 mV, and Det 2: +22 mV.

Data Analysis

Inhibition curves were fit to the two parameter logistic equation for the best-fit estimates of the IC50 using nonlinear least squares curve fitting methods as previously described (Rothman et al. (1993), supra); Jones, S. M. and Rogawski, M. A. *Mol. Neuropharmacol.* 2: 303–310 (1992)).

In vivo microdialysis data were analyzed by using a one-way ANOVA and post-hoc Dunnetts t-test. In the focal RTI experiments in which 3 drug concentrations were administered, the baseline value for dopamine was defined as the sample preceding the application of each drug concentration. Analysis of any drug effect was therefore made comparing the baseline value prior to the drug administration.

Results

RTI-4793-14

Table 1 lists the IC$_{50}$ values for PCP, (+)-MK801, and compounds 3a–e. (+)-MK801 binds with high affinity to PCP site 1 and low affinity to PCP site 2, whereas PCP binds with approximately the same potency at both sites. The 2-benzyl substituted compound 3b (RTI-4793-14) with IC$_{50}$ values of 37.9 nM and >20,000 nM for site 2 and site 1, respectively, is a potent and selective ligand for site 2. Compound 3b also was tested in the NovaScreen/NIMH Psychoactive Drug Discovery Program which included eleven neurotransmitter, four regulatory site, four ion channel, and three second-messenger assays. No significant inhibition was observed at 10$^{-5}$M for any of the assays. The 2-ethyl substituted compound 3e (RTI-4793-9) also is selective for site 2. However, its potency for site 2 is approximately ten-times less than that of 3b. Compound 3c (RTI-4793-13) which has a trimethylene bridge between the 1 and 2-positions of the ring system has an $IC_{50}$ of 2156 nM. The unsubstituted analogue 3a and compound 3e, which has a carboethoxy group in the 2-position, have low affinity at both sites. The results show that a 2-substituent is required for high potency at site 2 and that a benzyl group is better than an ethyl group.

TABLE 1

PCP (Site 1 and Site 2) Binding Properties of Indeno[1,2-b]pyrroles (3a–e).

| Compound | Code Name | PCP Site 2[a] $IC_{50}$ (nM) | PCP Site 1[a] $IC_{50}$ (nM) |
|---|---|---|---|
| 3a | RTI-4973-12 | >10,000 | >20,000 |
| 3b | RTI-4973-14 | 37.9 ± 5.7 | >20,000 |
| 3c | RTI-4973-13 | 2156 ± 383 | >20,000 |
| 3d | RTI-4973-7 | 16,691 ± 2498 | >20,000 |
| 3e | RTI-4973-9 | 326 ± 49 | >20,000 |
| — | PCP | 92.4 ± 7.0 | 117 ± 3 |
| — | (+)-MK801 | 15,917 ± 1974 | 4.58 ± 0.19 |

[a]The binding assays for PCP (site 2) and PCP (site 1) were conducted as previously reported (Rothman, R. B., et al., In: Multiple Sigma and PCP Receptor Ligands: Mechanisms for Neuromodulation and Protection 307–330 (Domino, E. F. and Kamenka, J. M., eds., 1992) using [$^3$H]TCP in the presence of (+)-MK801 for site 2 and [$^3$H]-MK801 for site 1 except that the [$^3$H]TCP assays were terminated after 18–24 hours of incubation at 4° C.

current responses (ffrench-Mullen, J. M. and Rogawski, M. A. J. *Neurosci.* 9:4051–4061 (1989)).

As observed by others (Hyttel, J. and Larsen, J. J. J. *Neurochem.* 44: 1615–1620 (1985)); Arnt, J., et al. *Naunyn Schmiedeberg's Arch. Pharmacol.* 329: 101–107 (1985)), indatraline potently inhibited [$^3$H]DA and [$^3$H]5-HT uptake, as well as [$^3$H]CFT binding to the DA transporter and [$^3$H]nisoxetine binding to the NE transporter. As is the case for other typical BAT ligands (Rothman et al. (1989), supra; Akunne et al. (1991), supra; Rothman et al. (1992), supra), indatraline had low micromolar affinity for PCP site 2 ($IC_{50}$, 2.5 μM), and negligible affinity for PCP site 1 ($IC_{50}$>100 μM). Consistent with its low affinity at PCP site 1, indatraline inhibited NMDA-induced current responses with very low potency.

RTI-4793-14 bound with high affinity to PCP site 2, and in addition, had moderate potency as an inhibitor of [$^3$H]DA uptake, [$^3$H]5-HT uptake, [$^3$H]CFT binding, and [$^3$H] nisoxetine binding. However, unlike PCP, RTI-4793-14 had low affinity for PCP site 1 ($IC_{50}$>36 μM) and low potency as inhibitor of NMDA-induced current responses.

TABLE 2

Interaction of RTI-4793-14 and Reference Compounds With NMDA Receptor- and Biogenic Amine Transporter-Related Indice

| Drug | PCP Site 2 $IC_{50}$ (nM ± SD) | PCP Site 1 $IC_{50}$ (nM ± SD) | BAT Related Measures | | | | NMD-A Induced Current $IC_{50}$ (μm) |
|---|---|---|---|---|---|---|---|
| | | | [$^3$H] 5-HT Uptake $IC_{50}$ (nM ± SD) | [$^3$H] DA Uptake $IC_{50}$ (nM ± SD) | [$^3$H] CFT Binding $IC_{50}$ (nM ± SD) | [$^3$H] Nisoxetine Binding $IC_{50}$ (nM ± SD) | |
| RTI-4793-14 | 37.9 ± 5.7 | >36,000 | 1024 ± 72 | 547 ± 20 | 850 ± 101 | 609 ± 48 | 768 |
| PCP | 92.4 ± 7.0 | 117 ± 3 | 1424 ± 81 | 347 ± 40 | >1500 | 16628 ± 98 | 2[1] |
| (+)-MK801 | >10,000 | 4.58 ± 0.19 | >4700 | >10000 | >15000 | 6576 ± 860 | 0.020[2] |
| Indatraline | 2529 ± 485 | >100,000 | 4.49 ± .21 | 3.23 ± .45 | 4.32 ± .46 | 2.27 ± 0.28 | 95 |

Synaptosomal uptake and ligand binding assays were conducted as described above. Preliminary experiments were conducted to determine the dose-range required for 10% to 90% inhibition. Each [$^3$H] ligand was displaced by 10 concentrations of test drug. The data of two experiments were pooled, and fit to the two parameter logistic equation for the best-fit estimates of the $IC_{50}$ reported above.
[1]ffrench-Mullen and Rogawski (1989), supra;
[2]Jones and Rogawski (1992), supra.

Figure 3:
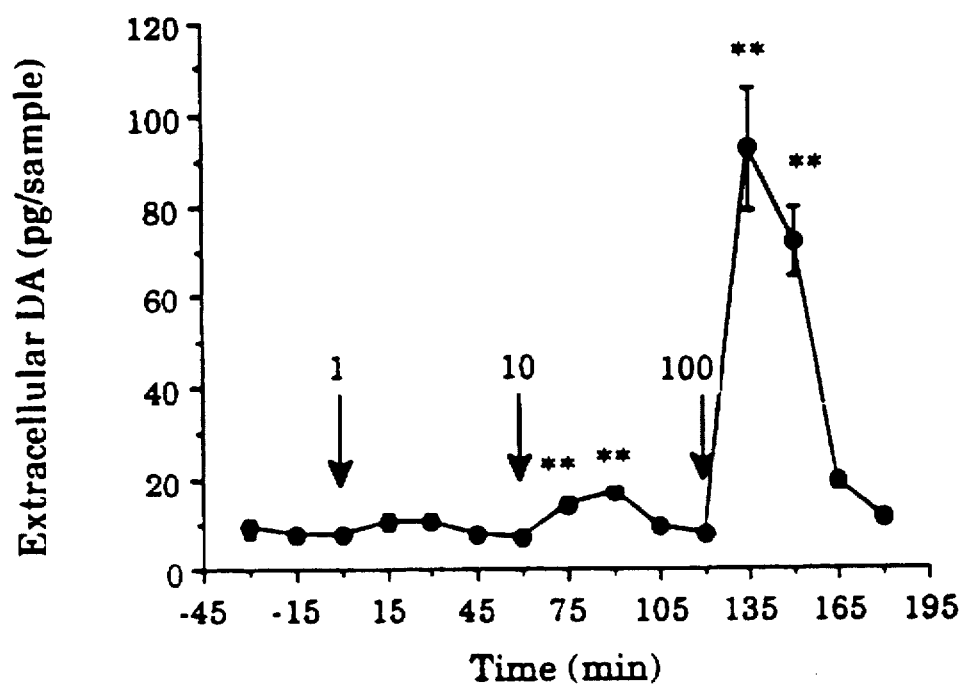
FIG. 3. In vivo microdialysis of extracellular dopamine in the nucleus accumbens at concentrations of 1, 10, and 100 µM of RTI-4793-14. All values are mean ±SEM (n=4). Group comparisons are made with one-way ANOVA and the Dunnetts t-test *p<0.05 and **p<0.01.
Figure 4:
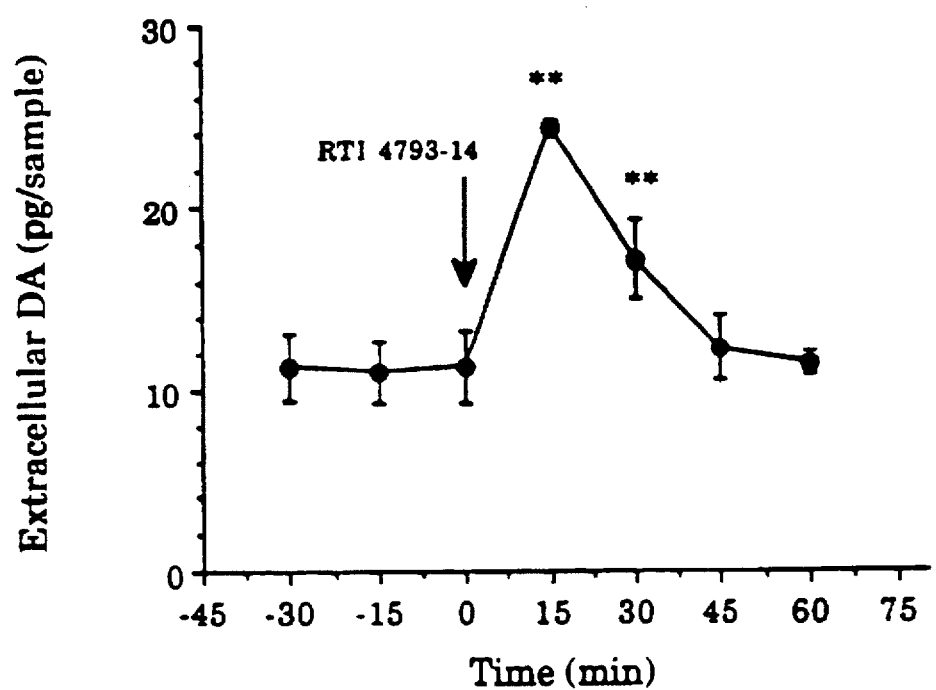
FIG. 4. Effects of systemic RTI-4793-14 (5 mg/kg, i.v.) on extracellular dopamine in the nucleus accumbens. All values are mean ± SEM (n=3). Group comparisons are made with one-way ANOVA and the Dunnetts t-test *p<0.05 and **p<0.01.

The $IC_{50}$ values of RTI-4793-14, PCP, (+)-MK801, and indatraline in the binding assays are presented in Table 2. As previously observed, PCP had moderate and about equal affinity for PCP site 1 and PCP site 2 (Rothman et al. (1989), supra). Also as observed by others (Smith, et al. (1977), supra), PCP inhibited [$^3$H]DA ($IC_{50}$, 347 nM) and [3H]5-HT ($IC_{50}$, 1424 nM) uptake with moderate potency. Consistent with its reported low affinity at the DA transporter labeled with [$^3$H]mazindol (Kuhar, M. J., et al. *Neuropharmacology* 29: 295–297 (1990)), PCP also had lower affinity at the [$^3$H]CFT binding site than would be predicted on the basis of its $IC_{50}$ for inhibition of DA uptake. PCP also had very low affinity for the NE transporter as labeled by [$^3$H] nisoxetine. Unlike PCP, (+)-MK801 had high affinity for PCP site 1, and negligible affinity for PCP site 2 and BAT-related measures. Consistent with its 25-fold greater potency at PCP site 1, (+)-MK801 has been shown to be much more potent than PCP in inhibiting NMDA-induced In vivo microdialysis experiments demonstrated that focal application of RTI-4793-14 via the microdialysis probe increased extracellular DA in a dose-dependent manner: 1 and 10 μM RTI-4793-14 increased extracellular DA by about 2- and 8-fold, respectively (FIG. 3). Additional experiments (FIG. 4) showed that intravenously administered RTI-4793-14 increased extracellular DA by about 2-fold.

RTI-4793-41 and RTI-4793-48, and Analogs Thereof

In vitro testing has demonstrated that RTI-4793-41 and RTI-4793-48 bind with high affinity to the MK801-insensitive (PCP site 2) binding site. The $IC_{50}$ value was determined to be 15 nM and 42 nM, respectively (Table 3). The (+) optical isomer of RTI-4793-41 was found to have an $IC_{50}$ value of 4.4 nM.

TABLE 3

Binding Data For The RTI-4793 Compounds at PCP Sites 1 and 2 in Guinea Pig Membranes.

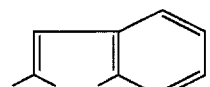

| Compound | Structure Type | R | X | PCP Site 1 IC$_{50}$ (nM) | PCP Site 2 IC$_{50}$ (nM) |
|---|---|---|---|---|---|
| RTI-4793-14 | C | C$_6$H$_5$ | — | >2000 | 37.9 ± 5.7 |
| RTI-4793-41 | A | C$_6$H$_5$ | — | >2000 | 15.6 ± 2.0 |
| RTI-4793-44 | C | 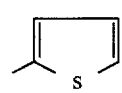 | — | >2000 | 114.1 ± 12 |
| RTI-4793-45 | C | p-ClC$_6$H$_4$ | — | >2000 | 254.2 ± 18 |
| RTI-4793-46 | C | p-CH$_3$OC$_6$H$_4$ | — | >2000 | 148 ± 23 |
| RTI-4793-47 | B | — | Br | >2000 | 68.8 ± 11.5 |
| RTI-4793-48 | B | — | H | >2000 | 42.3 ± 5.6 |
| RTI-4793-49 | A | p-CH$_3$OC$_6$H$_4$ | — | >2000 | 106.3 ± 13.8 |
| RTI-4793-50 | A | p-FC$_6$H$_4$ | — | >2000 | 73.5 ± 9.0 |
| RTI-4793-51 | A | CH$_2$C$_6$H$_5$ | — | >2000 | 289 ± 22 |
| RTI-4793-52 | A | (CH$_2$)$_3$C$_6$H$_5$ | — | >2000 | 302 ± 28 |
| RTI-4793-55 | A | (thiophene) | — | >2000 | 43.2 ± 6.58 |
| (−)-RTI-4793-41 | A | C$_6$H$_5$ | — | >2000 | 28.9 ± 3.0 |
| (+)-RTI-4793-41 | A | C$_6$H$_5$ | — | >2000 | 4.4 ± 0.7 |
| (−)-RTI-4793-14 | C | C$_6$H$_5$ | — | >2000 | 316.5 ± 58.7 |
| (+)-RTI-4793-14 | C | C$_6$H$_5$ | — | >2000 | 50.6 ± 7.9 |

Discussion

The results demonstrate that RTI-4793-14, RTI-4793-41, and RTI-4793-48 bind with high affinity and selectivity to the (+)-MK801-insensitive binding site (PCP site 2). Although most BAT ligands such as indatraline are selective for PCP site 2, they generally have low affinity for this site (K$_i$ values>1 µM). The only known exception is benztropine, which has a K$_i$ value of 183 nM at PCP site 2 (Rothman et al. (1992), supra). RTI-4793-14, which is at least 1000-fold selective for PCP site 2 versus PCP site 1, had the highest affinity for PCP site 2 of any of the drugs tested and is the first high affinity ligand to be described that clearly distinguishes between the two PCP binding sites. Like PCP, which has moderate potency in BAT-related measures, RTI-4793-14 inhibited E$^3$H]CFT binding and [$^3$H]5-HT and [$^3$H]DA uptake with moderate potency, but unlike PCP was a very low potency inhibitor of NMDA-induced current responses. Thus, RTI-4793-14 has a neurochemical profile similar to that of PCP, except that it is largely devoid of PCP site 1 activity and has considerably higher affinity at the NE transporter.

In accord with previous reports (Hyttel and Larsen (1985), supra; Arnt, et al. (1985), supra), indatraline was a potent inhibitor of [$^3$H]CFT binding, [$^3$H]nisoxetine binding, and [$^3$H]5-HT and [$^3$H]DA uptake (Rothman, et al. (1992), supra). However, as is typical of other previously investigated BAT ligands, the drug bound relatively weakly to PCP site 2. Although they both interact with biogenic amine transporters, RTI-4793-14, RTI-4793-41, and RTI-4793-48 were distinguished from indatraline in having substantially higher binding affinity for PCP site 2.

DA uptake blockers, including PCP (Carboni, E., et al. *Neuroscience* 28: 653–661 (1989)) and indatraline (Hurd, Y. L. and Ungerstedt, U. *Eur. J. Pharmacol.* 166: 261–269 (1989)) are known to increase extracellular DA levels. Consistent with its in vitro profile as a BAT inhibitor, RTI-4793-14 increased extracellular DA upon local or systemic administration in rats. The magnitude of the effect obtained with a 5 mg/kg IV dose was similar to that previously observed with a 1 mg/kg IV dose of cocaine, a potent DA uptake blocker (Hurd, Y. L. and Ungerstedt, U. *Synapse* 3: 48–54 (1989)). Thus RTI-4793-14 acts in vivo as well as in vitro as a biogenic amine transport blocker.

The high affinity and selectively of RTI-4793-14, RTI-4793-41, and RTI-4793-48, and analogs thereof for PCP site 2 suggests these compounds may be useful in radioligand binding studies to label this site with greater precision than is currently possible.

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A compound having the structure:

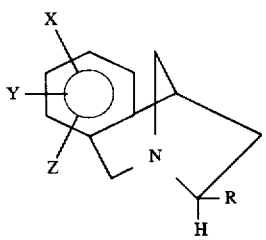

wherein X, Y, and Z are independently H, Cl, Br, F, OCH₃, I, or an alkyl group having 1 to 6 carbon atoms; and R is

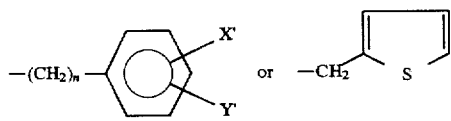

wherein n is 0 to 6, X' and Y' are independently H, Cl, F, CH₃, C₂H₅° C₃H₇, C₄H₉, OCH₃, OH, CF₃, OCF₃, NO₂, NH₂, N(CH₃)₂, NHCOCH₃, NCS, NHCOCH₂Br, or N₃, and (CH₂)ₙ, if present, may be substituted with OH, OCH₃, or an alkyl or alkenyl group having 1 to 3 carbon atoms.

2. The compound of claim 1, wherein R is a substituted or unsubstituted benzyl group.

3. The compound of claim 2, wherein X, Y, and Z are hydrogen.

4. The compound of claim 3, wherein R is benzyl.

5. The (+) optical isomer of the compound of claim 4.

6. The (−) optical isomer of the compound of claim 4.

7. The compound of claim 1, wherein R is a benzyl group substituted with fluoro or methoxy.

8. The compound of claim 1, wherein X, Y, and Z are hydrogen; and R is (CH₂)₂—C₆H₅.

9. The compound of claim 1, wherein X, Y, and Z are hydrogen; and R is (CH₂)₄—C₆H₅.

10. The compound of claim 1, wherein X, Y, and Z are hydrogen; and R is

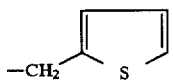

11. A pharmaceutical composition comprising the compound of claim 1 and a pharmaceutically acceptable carrier.

12. A method for treating a disease characterized by a dopamine deficiency which comprises administering to a subject in need of such treatment an amount of the pharmaceutical composition of claim 11 effective to treat the disease.

13. The method of claim 12, wherein the disease is Parkinson's disease or depression.

14. The method of claim 12, wherein the amount is between about 1 µg/kg and about 10 mg/kg.

15. A compound having the structure:

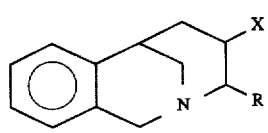

wherein X is H, Cl, Br, F, OCH₃, I, or an alkyl group having 1 to 6 carbon atoms; and R is

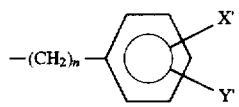

wherein n is 0 to 6, X' and Y' are independently H, Cl, F, CH₃, C₂H₅, C₃H₇, C₄H₉, OCH₃, OH, CF₃, OCF₃, NO₂, NH₂, N(CH₃)₂, NHCOCH₃, NCS, NHCOCH₂Br, or N₃, and (CH₂)ₙ, if present, may be substituted with OH, OCH₃, or an alkyl or alkenyl group having 1 to 3 carbon atoms.

16. The compound of claim 15, wherein R is phenyl.

17. The compound of claim 16, wherein X is bromo.

18. The compound of claim 16, wherein X is hydrogen.

19. A pharmaceutical composition comprising the compound of claim 15 and a pharmaceutically acceptable carrier.

20. A method for treating a disease characterized by a dopamine deficiency which comprises administering to a subject in need of such treatment an amount of the pharmaceutical composition of claim 19 effective to treat the disease.

21. The method of claim 20, wherein the disease is Parkinson's disease or depression.

22. The method of claim 20, wherein the amount is between about 1 µg/kg and about 10 mg/kg.

23. A pharmaceutical composition comprising the compound of claim 2 and a pharmaceutically acceptable carrier.

24. A pharmaceutical composition comprising the compound of claim 3 and a pharmaceutically acceptable carrier.

25. A pharmaceutical composition comprising the compound of claim 4 and a pharmaceutically acceptable carrier.

26. A pharmaceutical composition comprising the compound of claim 5 and a pharmaceutically acceptable carrier.

27. A pharmaceutical composition comprising the compound of claim 6 and a pharmaceutically acceptable carrier.

28. A pharmaceutical composition comprising the compound of claim 7 and a pharmaceutically acceptable carrier.

29. A pharmaceutical composition comprising the compound of claim 8 and a pharmaceutically acceptable carrier.

30. A pharmaceutical composition comprising the compound of claim 9 and a pharmaceutically acceptable carrier.

31. A pharmaceutical composition comprising the compound of claim 10 and a pharmaceutically acceptable carrier.

32. A method for treating a disease characterized by a dopamine deficiency which comprises administering to a subject in need of such treatment an amount of the pharmaceutical composition of claim 23 effective to treat the disease.

33. The method of claim 32, wherein the disease is Parkinson's disease or depression.

34. The method of claim 32, wherein the amount is between about 1 µg/kg and about 10 mg/kg.

35. A method for treating a disease characterized by a dopamine deficiency which comprises administering to a subject in need of such treatment an amount of the pharmaceutical composition of claim 24 effective to treat the disease.

36. The method of claim 35, wherein the disease is Parkinson's disease or depression.

37. The method of claim 35, wherein the amount is between about 1 µg/kg and about 10 mg/kg.

38. A method for treating a disease characterized by a dopamine deficiency which comprises administering to a subject in need of such treatment an amount of the pharmaceutical composition of claim 25 effective to treat the disease.

39. The method of claim 38, wherein the disease is Parkinson's disease or depression.

40. The method of claim 38, wherein the amount is between about 1 µg/kg and about 10 mg/kg.

41. A method for treating a disease characterized by a dopamine deficiency which comprises administering to a subject in need of such treatment an amount of the pharmaceutical composition of claim 26 effective to treat the disease.

42. The method of claim 41, wherein the disease is Parkinson's disease or depression.

43. The method of claim 41, wherein the amount is between about 1 82 g/kg and about 10 mg/kg.

44. A method for treating a disease characterized by a dopamine deficiency which comprises administering to a subject in need of such treatment an amount of the pharmaceutical composition of claim 27 effective to treat the disease.

45. The method of claim 44, wherein the disease is Parkinson's disease or depression.

46. The method of claim 44, wherein the amount is between about 1 µg/kg and about 10 mg/kg.

47. A method for treating a disease characterized by a dopamine deficiency which comprises administering to a subject in need of such treatment an amount of the pharmaceutical composition of claim 28 effective to treat the disease.

48. The method of claim 40, wherein the disease is Parkinson's disease or depression.

49. The method of claim 40, wherein the amount is between about 1 µg/kg and about 10 mg/kg.

50. A method for treating a disease characterized by a dopamine deficiency which comprises administering to a subject in need of such treatment an amount of the pharmaceutical composition of claim 29 effective to treat the disease.

51. The method of claim 50, wherein the disease is Parkinson's disease or depression.

52. The method of claim 50, wherein the amount is between about 1 µg/kg and about 10 mg/kg.

53. A method for treating a disease characterized by a dopamine deficiency which comprises administering to a subject in need of such treatment an amount of the pharmaceutical composition of claim 30 effective to treat the disease.

54. The method of claim 53, wherein the disease is Parkinson's disease or depression.

55. The method of claim 53, wherein the amount is between about 1 µg/kg and about 10 mg/kg.

56. A method for treating a disease characterized by a dopamine deficiency which comprises administering to a subject in need of such treatment an amount of the pharmaceutical composition of claim 31 effective to treat the disease.

57. The method of claim 53, wherein the disease is Parkinson's disease or depression.

58. The method of claim 53, wherein the amount is between about 1 µg/kg and about 10 mg/kg.

59. A pharmaceutical composition comprising the compound of claim 16 and a pharmaceutically acceptable carrier.

60. A pharmaceutical composition comprising the compound of claim 17 and a pharmaceutically acceptable carrier.

61. A pharmaceutical composition comprising the compound of claim 18 and a pharmaceutically acceptable carrier.

62. A method for treating a disease characterized by a dopamine deficiency which comprises administering to a subject in need of such treatment an amount of the pharmaceutical composition of claim 59 effective to treat the disease.

63. The method of claim 62, wherein the disease is Parkinson's disease or depression.

64. The method of claim 62, wherein the amount is between about 1 µg/kg and about 10 mg/kg.

65. A method for treating a disease characterized by a dopamine deficiency which comprises administering to a subject in need of such treatment an amount of the pharmaceutical composition of claim 60 effective to treat the disease.

66. The method of claim 65, wherein the disease is Parkinson's disease or depression.

67. The method of claim 65, wherein the amount is between about 1 µg/kg and about 10 mg/kg.

68. A method for treating a disease characterized by a dopamine deficiency which comprises administering to a subject in need of such treatment an amount of the pharmaceutical composition of claim 61 effective to treat the disease.

69. The method of claim 68, wherein the disease is Parkinson's disease or depression.

70. The method of claim 68, wherein the amount is between about 1 µg/kg and about 10 mg/kg.

* * * * *